US009474796B2

(12) United States Patent
Bergeron et al.

(10) Patent No.: US 9,474,796 B2
(45) Date of Patent: Oct. 25, 2016

(54) CRIMEAN-CONGO HEMORRHAGIC FEVER VIRUS VACCINE

(71) Applicant: Colorado Seminary, which owns and Operates The University of Denver, Denver, CO (US)

(72) Inventors: Eric Bergeron, Atlanta, GA (US); Scott Dusan Pegan, Denver, CO (US); Stuart T. Nichol, Atlanta, GA (US); Michelle Kay Deaton, Denver, CO (US)

(73) Assignees: The United States of America, as Represented by the Secretary, Department of Health and Human Services, Washington, DC (US); Colorado Seminary, which owns and operates the University of Denver, Denver, CO (US)

( * ) Notice: Subject to any disclaimer, the term of this patent is extended or adjusted under 35 U.S.C. 154(b) by 367 days.

(21) Appl. No.: 13/829,105

(22) Filed: Mar. 14, 2013

(65) Prior Publication Data

US 2014/0050761 A1    Feb. 20, 2014

Related U.S. Application Data

(60) Provisional application No. 61/683,132, filed on Aug. 14, 2012.

(51) Int. Cl.
*C12N 7/00* (2006.01)
*A61K 39/12* (2006.01)
*A61K 39/00* (2006.01)

(52) U.S. Cl.
CPC ....... *A61K 39/12* (2013.01); *A61K 2039/5254* (2013.01); *C12N 2760/12034* (2013.01)

(58) Field of Classification Search
None
See application file for complete search history.

(56) References Cited

U.S. PATENT DOCUMENTS

| 8,012,489 B2 | 9/2011 | Jones |
| 2003/0186431 A1 | 10/2003 | Torres |
| 2006/0057159 A1 | 3/2006 | Huang et al. |

FOREIGN PATENT DOCUMENTS

WO    2009/008924 A2    1/2009

OTHER PUBLICATIONS

Baker et al., Protein Structure Predication and Structural Genomics, Science (2001) vol. 294, No. 5540, pp. 93-96.*
Attwood, T. The Babel of Bioinformatics, Science (2000) vol. 290, No. 5491, pp. 471-473.*
Horning and Mayer. Regulation of AMPA receptor gating by ligand binding core dimers. Neuron. Feb. 5, 2004;41(3):379-88.*
Messaoudi and Basler. Immunological features underlying viral hemorrhagic fevers. Curr Opin Immunol. Jul. 7, 2015;36:38-46.*
International Search Report and Written Opinion for PCT Application No. PCT/US2013/054760 mailed Oct. 16, 2013.
Capodagli et al., "Diversity of Ubiquitin and ISG15 Specificity among Nairoviruses' Viral Ovarian Tumor Domain Proteases," Journal of Virology 87(7): 3815-3827 (2013).
James et al., "Structural Basis for the Removal of Ubiquitin and Interferon-Simulated Gene 15 by a Viral Ovarian Tumor Domain-Containing Protease," Proceedings of the National Academy of Sciences 108(6): 2222-2227 (2011).
Ambrosio, A., et al., "Argentine hemorrhagic fever vaccines," Human Vaccines, vol. 7, No. 6 (Jun. 2011) 7 pages.
Bergeron, E., et al., "Crimean-Congo hemorrhagic fever virus-encoded ovarian tumor protease activity is dispensable for virus RNA polymerase function," Journal of Virology, vol. 84, No. 1 (Jan. 2010) 11 pages.
Capodagli, GC, et al., "Diversity of ubiquitin and ISG15 specificity among nairoviruses's viral ovarian tumor domain proteases," Journal of Virology, vol. 87, No. 7 (Apr. 2013) 13 pages.
Capodagli, GC, et al., "Structural Analysis of a Viral Ovarian Tumor Domain Protease from the Crimean-Congo Hemorrhagic Fever Virus in Complex with Covalently Bonded Ubiquitin," Journal of Virology, vol. 85, No. 7 (Apr. 2011) 10 pages.
Carter, SD., et al., "Structure, function, and evolution of the Crimean-Congo hemorrhagic fever virus nucleocapsid protein," Journal of Virology, vol. 86, No. 20 (Aug. 2012) 10 pages.
Deyde, VM., et al., "Crimean-Congo Hemorrhagic Fever Virus Genomics and Global Diversity," Journal of Virology, vol. 80, No. 17 (Sep. 2006).
Dilcher, M. et al., "Genetic characterization of Erve virus, a European Nairovirus distantly related to Crimean-Congo hemorrhagic fever virus," Virus Genes, (2012) 7 pages.
Duh, D., et al., "The complete genome sequence of a Crimean-Congo hemorrhagic fever virus isolated from an endemic region in Kosovo," Virology Journal, vol. 5, No. 7 (Jan. 2008) 6 pages.
Keshtkar-Jahromi, M., et al., "Crimean-Congo hemorrhagic fever: current and future prospects of vaccines and therapies," Antiviral Res., vol. 90, No. 2 (May 2011) 8 pages.
Khan A, et al., "Viral Hemorrhagic Fevers," Seminars in Pediatric Infectious Diseases, vol. 8, No. 1 (Jan. 1997) 10 pages.
Martins, RM., et al., "17DD yellow fever vaccine: A double blind, randomized clinical trial of immunogenicity and safety on a dose-response study," Human Vaccines & Immunotherapeutics, vol. 9, No. 4 (Apr. 2013).
Schwedt, T. J. et al., "Thunderclap Headache," Lancet Neurology vol. 5, No. 7 (Jul. 2006) 10 pages.
Woessner, R. et al., "The Erve Virus: Possible Mode of Transmission and Reservoir," Infection vol. 28 (2000) 2 pages.
Yadav, P.D. et al, "Genomic analysis reveals Nairobi sheep disease virus to be highly diverse and present in both Africa, and in India in the form of the Ganjam virus variant," Infection Genetics and Evolution vol. 11 Issue 5, (Jul. 2011) 10 pages.

(Continued)

*Primary Examiner* — Michelle S Horning
(74) *Attorney, Agent, or Firm* — David Goetz; Kilpatrick Townsend & Stockton LLP

(57) ABSTRACT

The genetically modified hemorrhagic fever virus of this invention possesses a viral ovarian tumor protease with decreased ability to remove ubiquitin (Ub) and ISG15 tags that the human organism uses to label proteins for removal. Unlike complete knockout strains, the modified virus retains enough activity for replication in a human cell line. This creates an immunogenic and non-pathogenic virus that can be used as an effective live vaccine agent.

17 Claims, 9 Drawing Sheets

(56) References Cited

OTHER PUBLICATIONS

Akutsu, et al., "Molecular basis for ubiquitin and ISG15 cross-reactivity in viral ovarian tumor domains," *PNAS*, vol. 108, No. 6, pp. 2228-2233 (2011).

Bergeron, et al., "Crimean-Congo Hemorrhagic Fever Virus-Encoded Ovarian Tumor Protease Activity Is Dispensable for Virus RNA Polymerase Function," *J Virol.*, vol. 84(1), pp. 216-226 (2010).

Frias-Staheli, et al., "Ovarian Tumor Domain-Containing Viral Proteases Evade Ubiquitin- and ISG15- Dependent Innate Immune Responses," *Cell Host Microbe.*, vol. 2(6), pp. 404-416 (2007).

Holzer, et al., "Inhibition of Interferon Induction and Action by the Nairovirus Nairobi Sheep Disease Virus/Ganjam Virus," *PLoS ONE*, vol. 6(12), e28594, pp. 1-12 (2011).

Kasteren, et al., "Arterivirus and Nairovirus Ovarian Tumor Domain-Containing Deubiquitinases Target Activated RIG-I to Control Innate Immune Signaling," *J Virol.*, vol. 86(2), pp. 773-785 (2012).

Extended European Search Report for European Application No. 13829120.8 dated Feb. 25, 2016, 9 pages.

\* cited by examiner

A549 cells MOI 0.1

| | | |
|---|---|---|
| VTQVIDG | EEPPAKI | Afg09-2990 |
| VTQVIDS | EEPPAKI | Matin |
| VTQVIAG | EEPPAKI | Oman |
| VTQVIAG | EEPPAKI | Baghdad |
| VTQVIAG | EEPPAKI | UG3010 |
| VTQVIAS | EEPPAKI | Turkey |
| VTQVIAG | EEPPAKI | IbAr10200 |
| VTQVIAG | EEPPAKI | SPU128-81 |
| VTQVLAG | DEPPAKI | AP92Greece |

CCHV strains

| | | |
|---|---|---|
| WERVVDE | TEPEAVGT | DUGV |
| VTQVIAG | EEPPARLV | CCHFV |
| WEEVVPG | EEPEAKGI | NSDV |
| WEN.TEG | LEPEAIGL | ERVEV |
| WDSVSDI | TEPEAAAT | HAZV | other nairoviruses

CRIMEAN-CONGO HEMORRHAGIC FEVER VIRUS VACCINE

REFERENCE TO RELATED APPLICATIONS

This application claims the priority benefit of U.S. provisional application 61/683,132, filed Aug. 14, 2012. The priority application is hereby incorporated herein by reference in its entirety for all purposes.

GOVERNMENT SUPPORT

This invention was made in part with government support under NIH 1R03AI092249-01 awarded by the National Institutes of Health. The government has certain rights in the invention.

FIELD OF THE INVENTION

This application relates generally to the field of viral disease, prophylaxis, and vaccination. More specifically, it provides a virus vaccine modeled on the etiologic agent for Crimean-Congo hemorrhagic fever. It was produced by reducing the deubiquinating and deISGylating activities from the viral OTU protease.

BACKGROUND

Crimean-Congo hemorrhagic fever (CCHF) is a widespread tick-borne viral disease that can affect humans. It is a member of the Bunyaviridae family of RNA viruses. Clinical disease is rare in infected mammals, but it is commonly severe in infected humans. Outbreaks of illness are usually attributable to handling infected animals or people.

The causative organism is found in Asia, Eastern Europe, the Middle East, a belt across central Africa and South Africa and Madagascar. The main environmental reservoir and vector for the virus is hard ticks. Ticks carry the virus to domestic animal stock. Sheep, goats and cattle can develop viremia, but tend not to fall ill. Tick species that have been identified as infected with this virus include *Argas reflexus, Hyalomma anatolicum, Hyalomma detritum, Hyalomma marginatum* and *Rhipicephalus sanguineus.*

The onset of CCHF is sudden, with initial signs and symptoms including headache, high fever, back pain, joint pain, stomach pain, and vomiting. Red eyes, a flushed face, a red throat, and petechiae (red spots) on the palate are common Symptoms may also include jaundice, and in severe cases, changes in mood and sensory perception. As the illness progresses, large areas of severe bruising, severe nosebleeds, and uncontrolled bleeding at injection sites can be seen, beginning on about the fourth day of illness and lasting for about two weeks.

Animal herders, livestock workers, and slaughterhouses in endemic areas are at risk of CCHF. Healthcare workers in endemic areas are at risk of infection through unprotected contact with infectious blood and body fluids. Individuals and international travelers with contact to livestock in endemic regions may also be exposed. In documented outbreaks of CCHF, fatality rates in hospitalized patients have ranged from 5% to as high as 80%.

Previous attempts to develop preventative treatment are as follows. In a USSR/Bulgarian CCHF vaccine developed in 1974 comprised an inactivated antigen from CCHF virus strain V42/81. It was generated from suckling mouse brain preparations, and so is unsuitable for FDA approval in the U.S. There is also a recombinantly produced construct comprising G1 (Gc), or G2 (Gn) glycoprotein ectodomains or portions thereof. However, no study exists to suggest any efficacy for this approach. Full effectiveness of this construct may be limited to the specific strain where the selected glycoproteins originated. There is no established virus-specific treatment. Ribavirin is thought to be effective in vitro, and has been used in human subjects during outbreaks. There are conflicting reports as to effectiveness, with the more recent ones showing limited to no effectiveness against CCHF virus in vivo.

The Department of Defense views CCHF virus as a potential threat to the U.S. armed forces when operating in countries endemic to the virus. These geographical locations include but are not limited to Afghanistan, Pakistan, and the Middle East. The need for preventative treatment of was underscored by death of a U.S. soldier from CCHF viral infection in 2009.

SUMMARY OF THE INVENTION

This invention provides a genetically modified hemorrhagic fever virus that has a viral ovarian tumor protease with decreased ability to remove ubiquitin (Ub) and ISG15 tags from proteins in the cells it infects. Unlike complete knockout strains, the modified virus retains enough activity for replication in a human cell line. This creates an immunogenic and non-pathogenic virus that can be used as an effective live vaccine agent.

One aspect of this invention is a pharmaceutical composition effective in eliciting a specific immune response, that is capable of replication in human cells, but that has been recombinantly altered to have decreased deubiquinating activity or decreased deISGylating activity while maintaining protease activity. Any hemorrhagic fever virus, nairovirus, or a member of the Bunyaviridae family of RNA viruses can be tested for suitability of this invention. A non-limiting example is Crimean-Congo hemorrhagic fever (CCHF) virus, which is used to illustrate the more general aspects of the invention in this disclosure.

Immunogenic compositions of this type can be recombinantly altered to have decreased deubiquitinating activity and/or decreased deISGylating activity. Typically, a lower level of deubiquitinating activity and a lower level of deISGylating activity remain in the mutant virus so that the virus can replicate in a suitable host cell: for example, less than 10%, 5%, or 2% of the activity of either or both deubiquitinating activity and deISGylating activity.

By way of illustration, the immunogenic composition may be modified at position 13, position 77, or both position 13 and 77 of the L-protein. Position 13 of the L-protein may be changed to arginine; position 77 may be changed to aspartic acid. The immunogenic composition may further comprising an adjuvant. After modification, the vOTU protein may have no ability or a reduced ability to inhibit expression of interferon β.

A related aspect of the invention is a recombinant CCHF virus that has been modified to have both decreased deubiquinating activity and decreased deISGylating activity, and that is capable of replication in human cells. The invention includes other viruses that have been recombinantly engineered or mutated to reduce deubiquinating and deISGylating activity. This includes Dugbe virus (DUGV), Hazara (HAZV), Nairobi sheep disease virus (NSDV), Ganjam virus (GANV), or any virus that causes febrile illness of varying severity in humans, pets, and agricultural animals.

Included in the invention are host cells transfected with an engineered virus having one or more of the properties indicated above.

Another aspect of the invention are methods for eliciting a specific immune response and/or for preventing or treating hemorrhagic fever, using a recombinant virus or immunogenic composition. Also provided are methods for preparing a commercial product wherein a composition or virus is packaged with information on use.

This invention also provides a method of developing an immunogenic but substantially non-pathogenic hemorrhagic fever virus. A host cell is transfected with the genome of a wild-type hemorrhagic fever virus along with genetic material comprised of a codon optimized L-protein. The genome has one or more genetic alterations introduced before transfection. Viral particles are recovered, and then tested and selected for decreased deubiquitinating activity and/or decreased deISGylating activity. The method may entail transfecting the host cell with the L, M, and S gene sectors in separate vectors.

Another aspect of the invention is a method for preparing a commercial product. A vaccine or pharmaceutical composition of the invention is packaged with information on how to use the product for eliciting an immune response or for preventing or treating hemorrhagic fever.

Other aspects of the invention will be apparent from the description that follows.

DESCRIPTION OF THE DRAWINGS

FIG. 1 depicts structural features of CCHF virus and other nairovirus related diseases.

FIG. 4 shows the reverse genetics method developed to produce recombinant CCHF virus in T7 RNA pol. expressing cells.

FIG. 7 shows results of an assay for interferon (IFN) beta (β) in cells infected with CCHF virus wild type (WT) and the selected mutant.

FIG. 8 shows results of monitoring ISGylation of wild type (wt) CCHF virus and reverse genetically produced CCHF virus containing the I13R/P77D mutation.

FIG. 13 compares the three-dimensional structure of the vOTU protein in CCHF and Dugbe nairoviruses.

FIG. 14 shows that residues P77 and I13 are highly conserved amongst strains of CCHFV (SEQ ID NOS:4-12) (top) and other nairoviruses (SEQ ID NOS:13, 14, 7 and 15-21) (bottom), particularly those known to cause human disease.

DETAILED DESCRIPTION

Context

Figure 2:
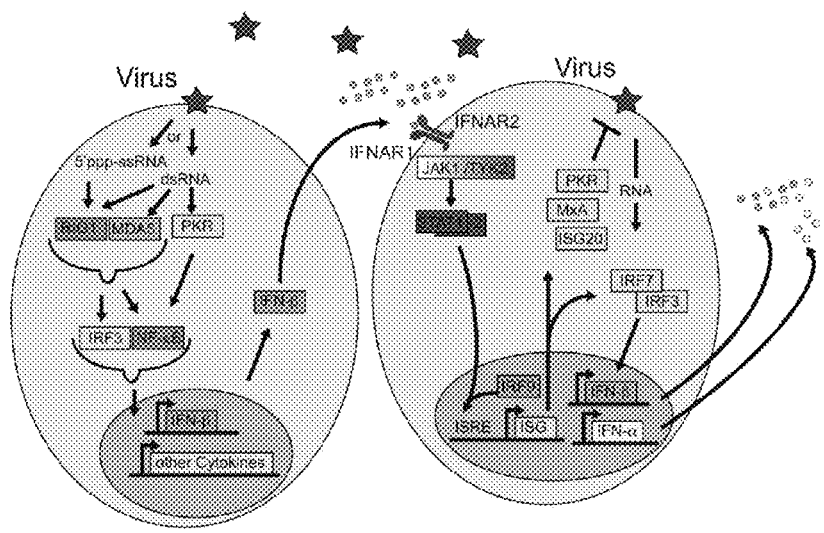
FIG. 2 illustrates the molecular pathway and modulation of the innate interferon (IFN) type 1 mediated immune response.

The Crimean-Congo hemorrhagic fever (CCHF) virus is a member of the genus Nairovirus, family Bunyaviridae. The negative sense RNA genome is composed of three segments—Small (S), Middle (M) and Large (L). The L segment is 11-14.4 kilobases in length while the M and S segments are 4.4-6.3 and 1.7-2.1 kilobases long respectively. The L segment encodes the RNA polymerase; the M segment encodes the envelope proteins (Gc and Gn); and the S segment encodes the nucleocapsid protein. The envelope protein is initially translated as a glycoprotein precursor which is then cleaved into the mature structural glycoprotein products (Gn and Gc) and non-structural glycoproteins.

CCHFV is not the only nairovirus that causes human disease. Dugbe virus (DUGV), Hazara (HAZV), Nairobi sheep disease virus (NSDV), and Ganjam virus (GANV) all result in varying severity of febrile illness and are located in a subset of countries within the CCHFV endemic region. Additionally, infection with NSDV and the closely related GANV in sheep negatively impacts local economies through high livestock mortality and limiting of trade with the affected areas. ERVV, found in Germany, France, Netherlands, and the Czech Republic, is increasingly implicated as the causative agent of severe headaches, known as thunderclap headaches, which result from subarachnoid hemorrhages in humans.

Further information about these viruses is provided by Yadav, P. D. et al., Infect Genet Evol 11, 1111-1120, 2011; Dilcher, M. et al., Virus Genes, Aug. 7, 2012; Schwedt, T. J. et al., Lancet Neurol 5, 621-631, 2006; and Woessner, R. et al., Infection 28, 164-166, 2000. Further information on the CCHF virus as a model for other viruses in this family, including its structure, and biology, can be found in the following publications: Khan A, et al. Viral Hemorrhagic Fevers. Seminars in Pediatric Infectious Diseases. Philadelphia: WB Saunders Co., 1997; 8 (suppl 1):64-73; Peters C J. Viral Hemorrhagic Fevers. Viral Pathogenesis. New York: Lippincott-Raven Publishers, 1997:779-794.

Ubiquitin is a small intracellular protein that becomes conjugated to and marks proteins for destruction or for transport to particular compartments inside the cell. Ubiquitination is an enzymatic post-translational modification process in which the carboxylic acid of the terminal glycine in activated ubiquitin is catalyzed to form an amide bond to the epsilon amine of the lysine in the modified protein.

Interferon-induced 17 kDa protein ISG15 is a protein that is expressed in response to interferon. ISG15 shares several properties with other ubiquitin-like molecules. Its activity is tightly regulated by specific signaling pathways that have a role in innate immunity. It also has cytokine activity. The mechanism of ISGylation is similar to that of ubiquitination.

Wild-type hemorrhagic fever viruses have both deubiquinating and deISGylating activity to reverse labeling by ubiquitin and ISG15 as part of its arsenal of weaponry that it brings to bear upon infection of the host.

Overview of the Invention

It has now been discovered that impairment but not elimination of the ability of the virus to remove ubiquitin (Ub) and ISG15 tags creates an immunogenic and non-pathogenic virus that can be used as an effective live vaccine agent.

Post-translational modification of host proteins by ubiquitin (Ub) and Ub-like interferon simulated gene product 15 (ISG15) known as ubiquitination and ISGylation, respectively, is a way that the human organism tags proteins for removal and degradation. Ubiquitin is a small regulatory protein found in almost all tissues that directs protein recycling by attaching to proteins and labeling them for destruction. The ubiquitin tag directs proteins to the proteasome, which is a large protein complex in the cell that degrades and recycles unneeded proteins. Interferon-induced 17 kDa protein is a protein that in humans is encoded by the ISG15 gene. ISG15 shares several common properties with other ubiquitin-like molecules (UBLs), but its activity is tightly regulated by specific signaling pathways that have a role in innate immunity Upon interferon treatment, ISG15 can be detected in both free and conjugated forms, and is secreted from monocytes and lymphocytes where it can function as a cytokine.

CCHF virus and all other nairoviruses including Dugbe virus (DUGV), Hazara (HAZV), Nairobi sheep disease virus (NSDV), and Ganjam virus (GANV) possesses a protease (specifically, the viral ovarian tumor domain protease) that performs deubiquitination and deISGylation functions. This enables the virus to evade the human immune response by down-regulating immunological functions such as expression of interferon as well as other antiviral effector and signaling proteins. However, complete loss of function of this protease results in the inability of CCHF virus and likely other nairoviruses to replicate. This prevents viruses that have been genetically modified to eliminate these activities entirely from being useful as a self-propagating vaccine agent.

The genetically modified virus of this invention possesses a viral ovarian tumor protease with significantly less deubiquitination and deSIGylation activity, while still retaining enough activity for virus production in a human cell line. The modified virus will not efficiently evade the human immune response, but will generate a level of immunity in the host that protects against future infection by a wild-type virus.

Development of Modified Strains of Virus

The invention described in this disclosure was developed using recombinantly sourced Crimean-Congo hemorrhagic fever virus as a model. The model CCHF virus strain was recovered from hamster cell line (BSR/T7) and propagated in human cell lines. Selective mutations were generated that result in the simultaneous ablation of the greater than 95% deubiquinating and deISGylating in vitro activity of virus's viral ovarian tumor domain protease.

Reverse genetic derived infectious Crimean-Congo hemorrhagic fever virus strain IbAr10200 may be achieved by first cloning the originating virus's cDNA, or by completing gene synthesis, of the complete segments (S, M and L). The S, M, and L segments were cloned in the pT7 vector between a T7 promoter, to drive the transcription of Crimean-Congo hemorrhagic fever virus complementary genome RNA copies, and a hepatitis D ribozyme, to obtain authentic 3' termini. The vectors were transfected into BSR/T7 cells to obtain recombinant RNA genome matching the cloned sequence. Complementation of the with mammalian expression vectors pCAGGS encoding a human codon optimized L-protein (pC-L) and wild-type N protein (pC-N) is used to obtain recombinant virus.

Details were as follows: Wild recombinant CCHF virus was rescued by transfecting a 10 cm² well of subconfluent BSRT7/5 cells with 2.5 µg pT7-S, 1 µg pT7-M, 1 µg pT7-L, 0.66 µg of pC-N and 0.33 µg of human codon optimized pC-L mixed with 11 µL of Mirus LT1™ transfection reagent (Mirus Bio LLC, Madison, Wis.) in OPTI-MEM™ media. All viruses recovered were harvested from cell supernatants four days post transfection and amplified in SW13 cells.

A CCHF vOTU expression construct was obtained by use of an *Escherichia coli* BL21 codon-optimized synthesis of the first 169 amino acids from the L protein in CCHF virus (GenBank accession no. AAQ98866.2) by Biobasic, Inc. Along with the vOTU portion of the L protein, six histidine codons and a stop codon were added to the gene in order to provide a C terminus histidine tag. The resulting gene was incorporated into a pET11a plasmid using NdeI and BamHI restriction sites. Site directed mutagenasis of the construct was performed using a QuikChange™ kit. Successful mutations were confirmed by sequencing performed by Genscript™. The mutated constructs were then transformed into BL21(DE3) cells, and were grown at 37° C. in 6 L of LB broth containing 100 µg/mL of ampicillin until the optical density at 600 nm reached 0.6. Expression of wild type (WT) or mutant CCHF vOTU was induced by the addition of IPTG to a final concentration of 0.8 mM. The culture was further grown for 4 hrs at 37° C. and then centrifuged at 6,000×g for 10 minutes. Cells were collected and stored at −80° C. until use. vOTUs were purified according to a standard protocol and assayed for activity.

CCHFV L amino acid positions 13 and 77 were mutated to isoleucine and aspartic acid and replaced the wild type pT7-L vector in the transfection plasmid mix. Four days following the transfection, immunoreactive foci can be detected and recovery of infectious recombinant Crimean-Congo hemorrhagic fever virus was confirmed by passing the transfection supernatants to SW13 cells. Three days later, cytopathic effect can be evident and Crimean-Congo hemorrhagic fever virus antigens can be detected throughout a cell monolayer.

Mutation of the 13$^{th}$ and 77$^{th}$ amino acid positions within their L-protein to isoleucine and aspartic acid respectively create a mutant lacking significant Ub and ISG15 activity, while maintaining activity to cleave a peptide. Aberration of complete activity of the viral ovarian tumor domain protease that is located in 1-169 amino acids of the L-protein by a mutation of position 40 from cysteine to alanine results in no recombinant virus.

Mutation of position 77 of the L-protein to aspartic acid results in the viral ovarian tumor protease of Crimean-Congo hemorrhagic fever virus strains is necessary to disrupt a hydrophobic interaction between it and human interferon stimulated gene product 15. This significantly reduces the ability of the viral ovarian tumor protease to recognize stimulated gene product 15.

To remove deubiquitinating activity, mutation of position 13 of the L-protein to arginine interferes through charge repulsion with an arginine at position 42 in ubiquitin and a tryptophan at position 123 in interferon stimulated gene product 15. This double mutation reduces deubiquitinating and deISGylating activities to 2% and 3% that of wild-type viral ovarian tumor protease, respectively, while maintaining catalytic activity greater than 88% that of wild-type viral ovarian tumor protease in vitro.

To construct the recombinant virus, the gene encoding native L-protein is altered at position 77 and position 13 of the amino acid sequence to delete the residue or substitute a residue or plurality of residues that is different from the native sequence. For example, the amino acid substitution at position 13 in the L-protein could be lysine or histidine. The amino acid substitution at position 77 in the L-protein could be other amino acids with a polar or charged side chain.

The I13R/P77D double mutation eliminates CCHF virus's viral ovarian tumor (vOTU) domain protease from performing deubiquitinating and deISGylating activity, but it still allows the virus to replicate. The CCHF virus with the I13R/P77D changes maintains one or more critical innate immunity biomarkers.

Illustrations

Figure 1:
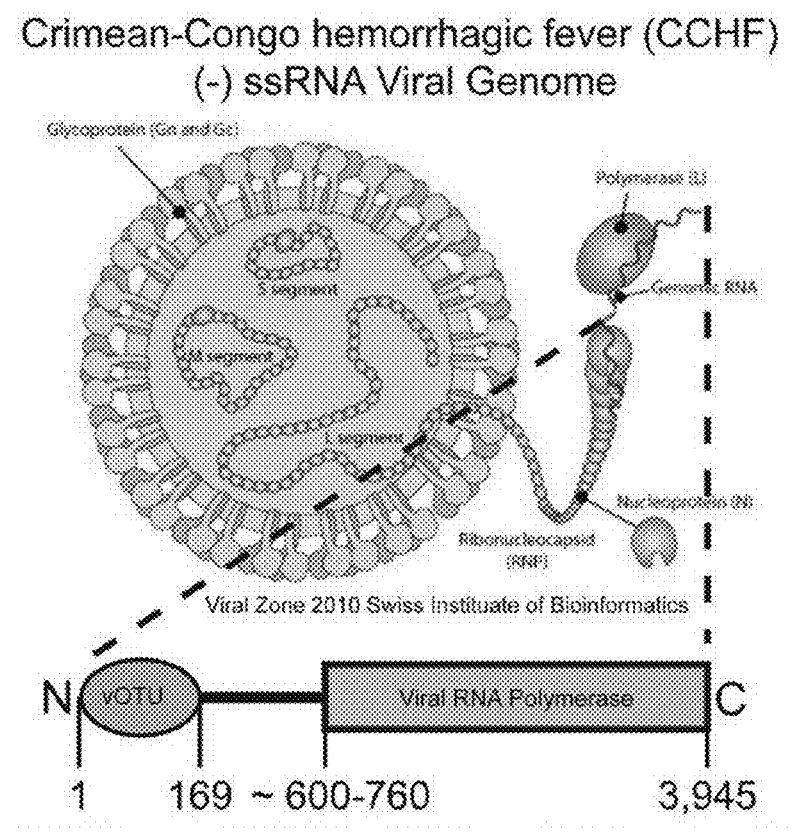

FIG. 1 depicts structural features of CCHF virus and the etiologic agent for other nairovirus related diseases. Rift Valley Fever Virus possesses an S-segment encoded NSs virulence factor, which allows for immune system evasion. Removal of NSs results in virus that does not effectively evade immune system. Crimean-Congo hemorrhagic fever (CCHF) virus does not encode a NSs factor, but it does have a vOTU (Viral Ovarian Tumor Domain Protease: see G C Capodagli et al., J Virol. 2011 April; 85(7): 3621-3630).

FIG. 2 illustrates the molecular pathway and modulation of the innate interferon (IFN) type 1 mediated immune response.

Figure 3:
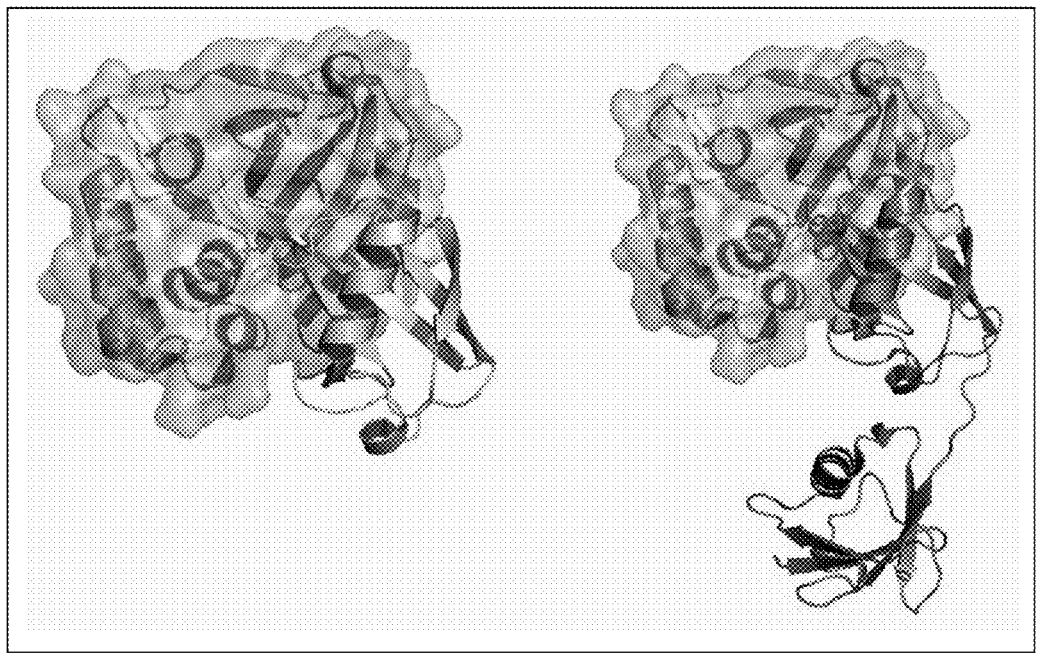
FIG. 3 is a three-dimensional representation of the ubiquitin and ISG15 proteins docking with the Viral Ovarian Tumor Domain Protease (vOTU) of CCHF virus.

FIG. 3 is a three-dimensional representation of the ubiquitin and ISG15 proteins docking with the vOTU protein of CCHF virus, developed from the crystal structure of CCHF virus determined by Capodagli et al. supra.

Figure 4:
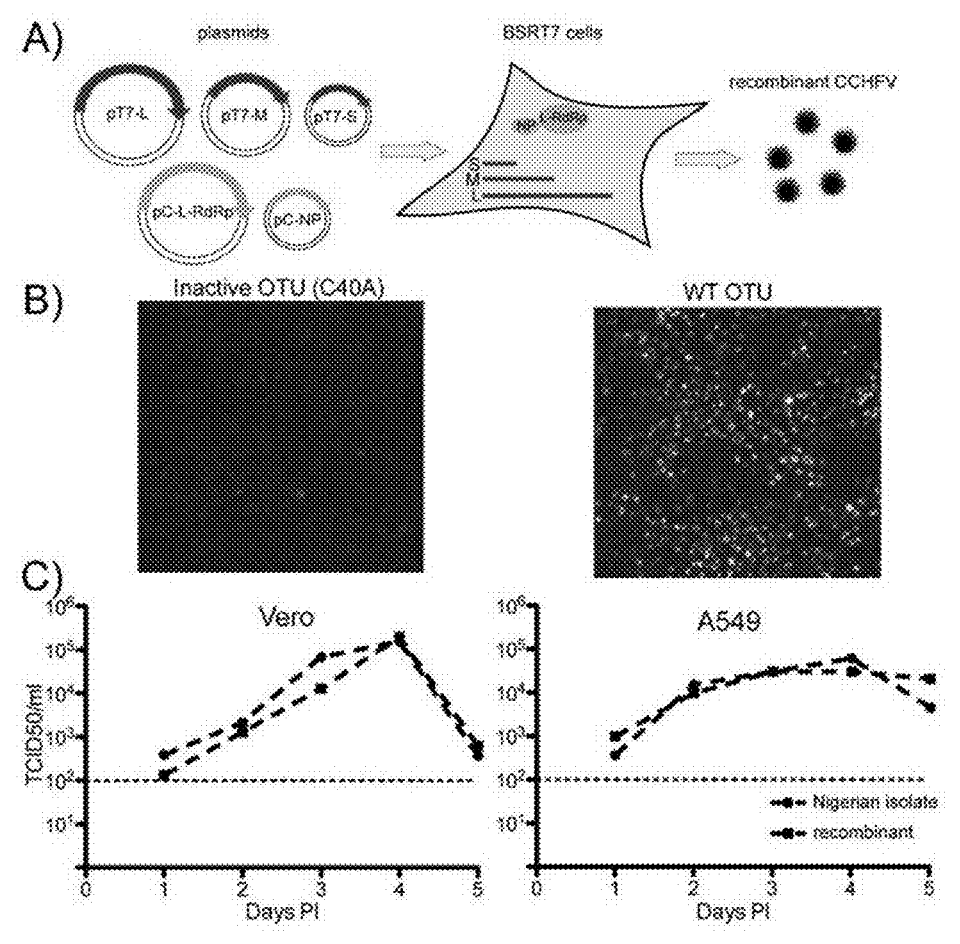
Figure 5:
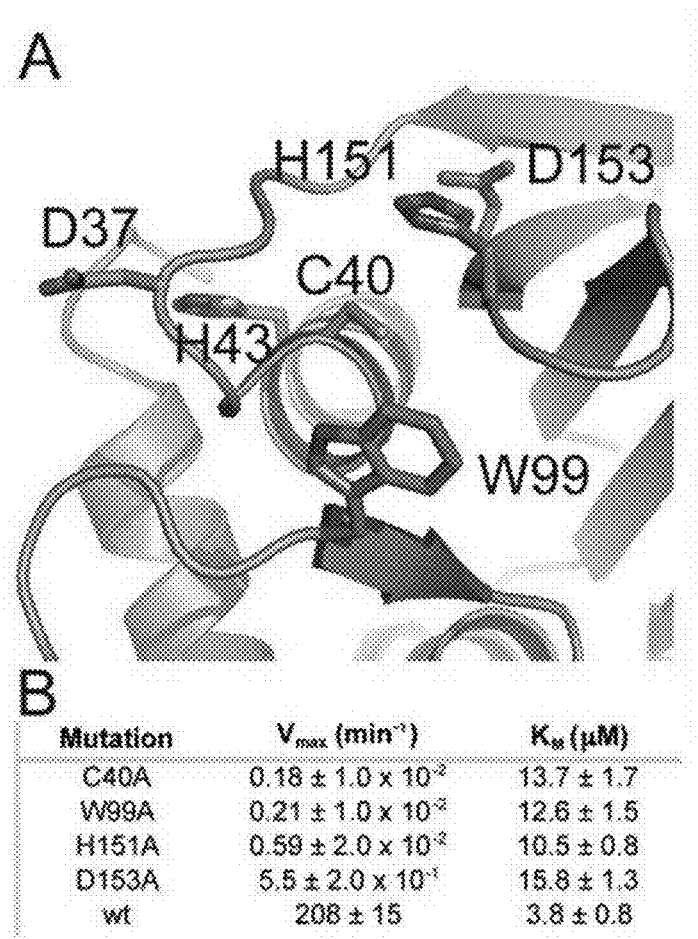
FIG. 5 depicts the active site of vOTU as a three-dimensional rendering.

FIGS. 4 and 5 show the reverse genetics CCHF virus system used for developing the invention. FIG. 4(A) shows the method developed to produce recombinant CCHF virus in T7 RNA pol. expressing cells. The solid arrows depict the genome RNA produce by the T7 ("pT7"), and viral proteins supporting the initial genome replication ("pC"). The panels below show immunofluorescence detection of CCHF virus produced by reverse genetics.

FIG. 5 depicts the active site of vOTU. (A) is a three-dimensional rendering of vOTU's active site, showing secondary structures, helices, and loops. (B) Mono-Ub Km and Vmax constants determined for catalytic triad vOTU mutants.

Figure 6:
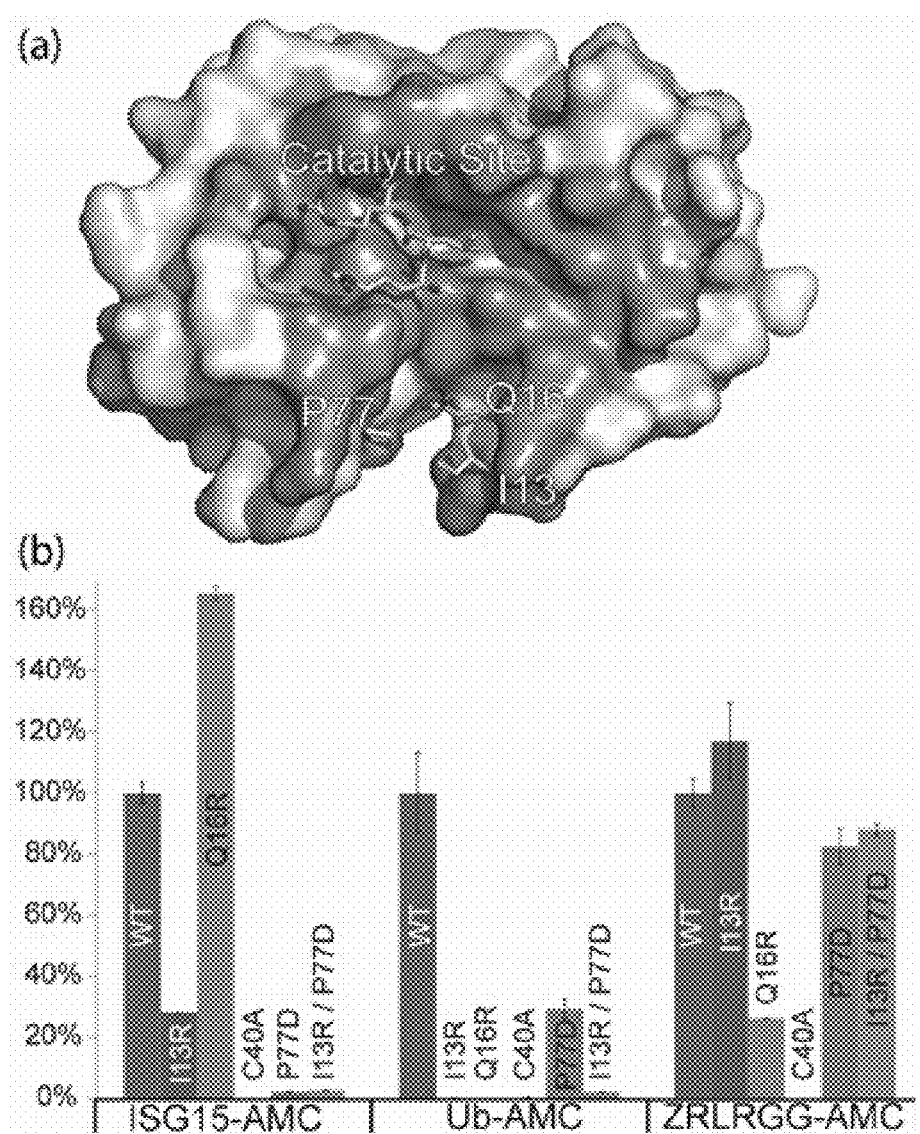
FIG. 6(a) shows the residues selected for mutation as part of the three-dimensional structure of vOTU.
FIG. 6(b) presents data showing disruption of the vOTU deubiquinating and deISGylating activities in vitro

FIG. 6 is taken from the development of CCHF virus vOTU-I13R/P77D. FIG. 6(a) shows data from disruption of the vOTU deubiquitinating and deISGylating activities in vitro. The CCHF virus vOTU is shown with the residues which comprise the complete vOTU/Ub binding interface. Residues Q16 and I13 were selected to disrupt the binding of Ub through site directed mutagenesis. P77 was selected to disrupt peptide binding of ISG15 through mutagenesis. The peptide RLRGG represents the C-terminal tail of Ub and ISG15. FIG. 6(b) shows data from disruption of the vOTU deubiquitinating and deISGylating activities in vitro.

Figures 7, 8:
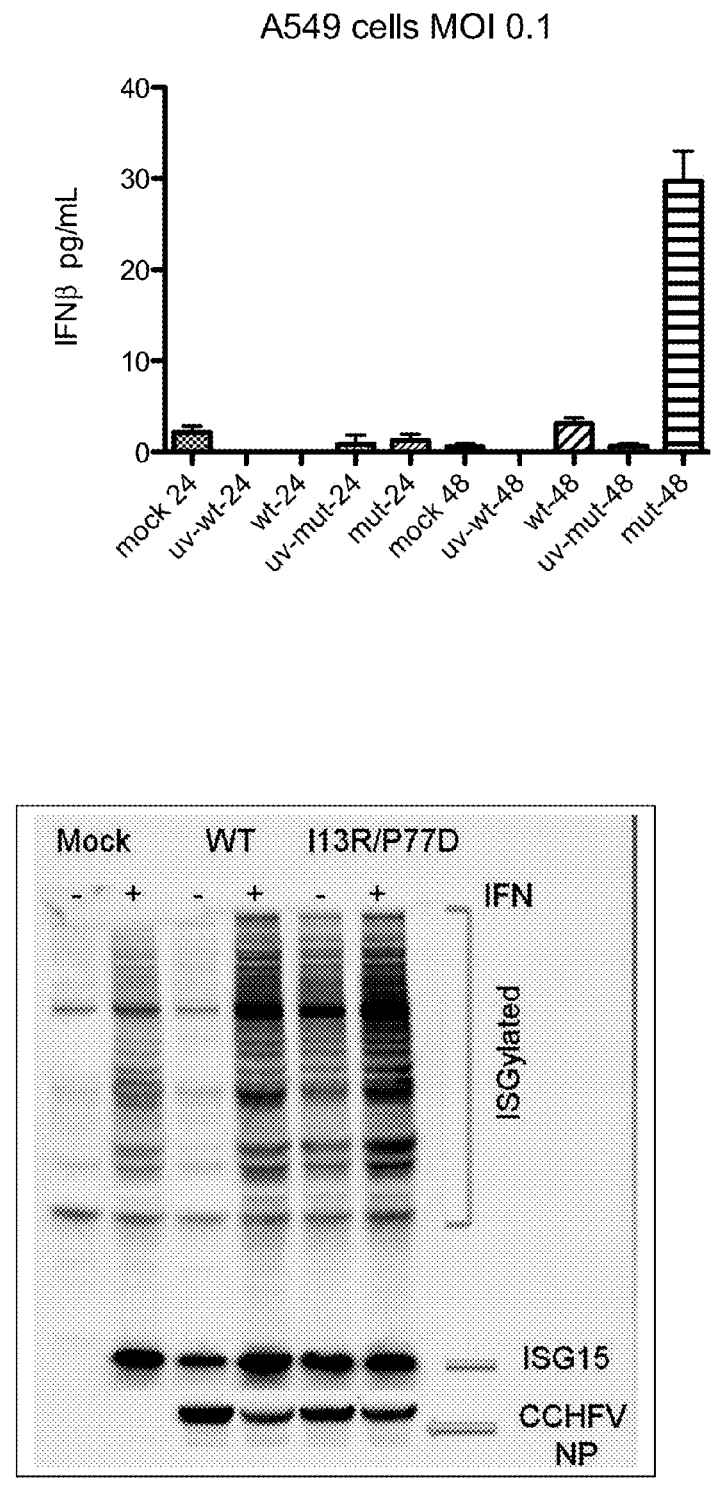

In FIG. 7 interferon (IFN) β was monitored from immunocompetent A549 cells that were infected with UV inactivated wt CCHF virus (uv-wt), wt CCHF virus (wt), I13R/P77D CCHF virus (mut). Upon infection, bsrt7 cells are not interferon producing cells, whereas A549 are. 24 and 48 denotes the time points for surveying IFN β production. For uv-wt, the virus is inactivated and incapable of infection, thus no IFN β production. Wild type CCHF virus has a functioning vOTU that suppresses IFN β production. However, I13R/P77D renders CCHF virus's vOTU unable of performing that function resulting in a significantly observable change in IFN β level over 48 hours.

FIG. 8 shows results of monitoring ISGylation of wild type (wt) CCHF virus and reverse genetically produced CCHF virus containing the I13R/P77D mutation within CCHF virus's vOTU. ISG15 antibodies were used to highlight proteins that have been ISGylated within A549 cells upon mock infection or infection by wt CCHF virus or I13R/P77D CCHF virus. Antiserum specific for CCHF nucleocapsid was used as a control to confirm CCHF virus infection. As mock infection contains no virus, no significant ISGylation occurs. Infection of wt CCHF virus reduces the ISGylation to mock levels where as the CCHF virus containing the I13R/P77D mutation can't reduce intracellular ISGylation levels. The (+) columns denote addition of exogenous interferon to probe to evaluate the extent of CCHF virus vOTU activity.

Figure 9:
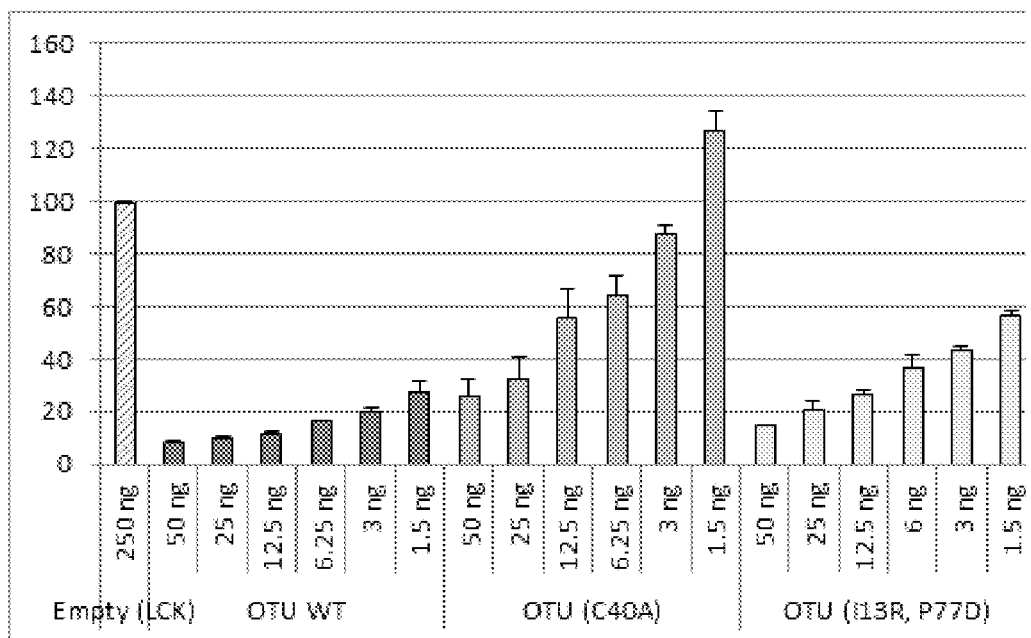
FIG. 9 shows data comparing the ability of the engineered virus with a totally inactive mutant virus (C40A) to inhibit production of interferon beta.
Figure 10:
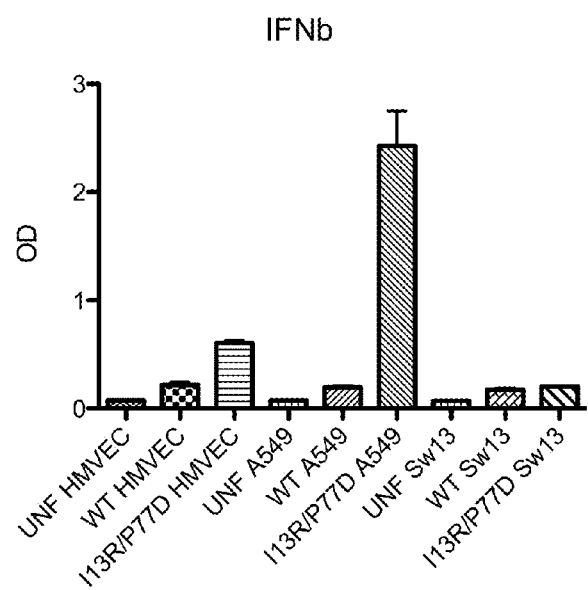
FIG. 10 shows a test for interferon β production in lung carcinoma A549 cells

FIG. 9 shows the reduced ability of transfected I13R/P77D at suppressing the transcription activation of an interferon β promoter relative to a totally inactive mutant (C40A) and wild type (WT) vOTU in human embryonic kidney 293 cells. FIG. 10 shows that I13R/P77D CCHFV lack of ability to suppress human immunity (as measured by interferon β production) is lung carcinoma A549 cells and primary culture of human microvascular endothelial cells (HMVEC).

Figure 11:
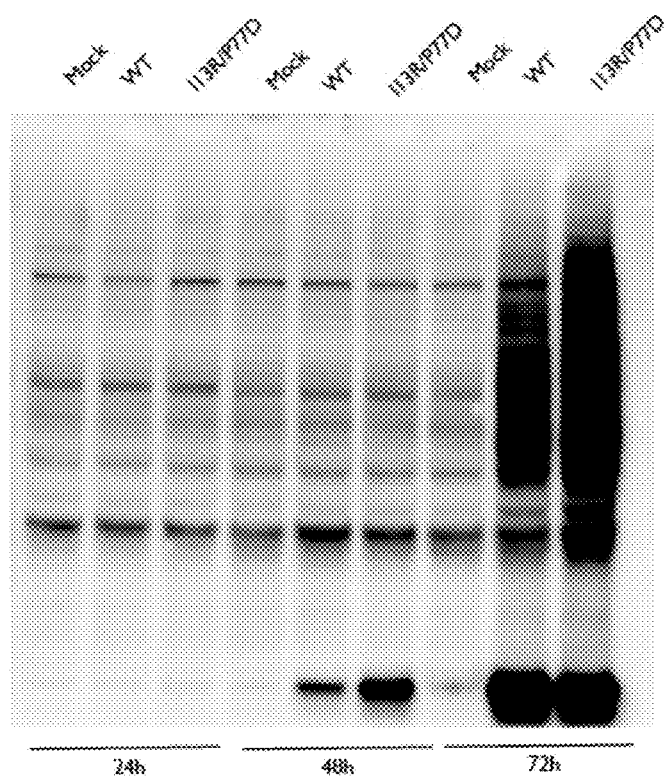
FIG. 11 shows a Western blot testing human ISG15 activity.
Figure 12:
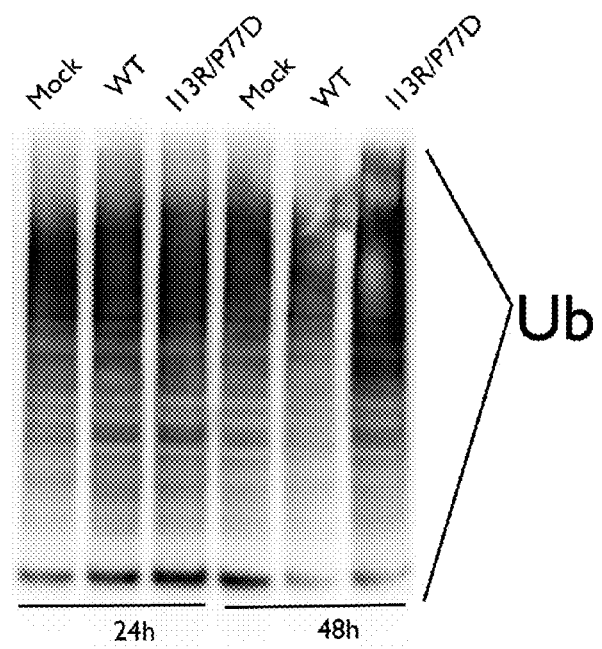
FIG. 12 shows a Western blot of the total levels of cellular protein ubiquitination in cells following infection.

FIG. 11 shows a Western blot for human ISG15 in A549 cells infected with wt CCHFV or I13R/P77D. Mock-infected lanes are also included. Cells infected with I13R/P77D have a significantly higher concentration of ISG15 conjugated proteins (the proteases substrate), then WT (wild type). The mock infected cells have no virus in them, and establish a basal level for ISG15 activity in this assay. FIG. 12 shows a Western blot of the total levels of cellular protein ubiquitination in A549 cells following WT and I13R/P77D infection. This indicates that ubiquitination level is enhanced only by the I13R/P77D infection after 48 h.

FIG. 13 shows the crystal structure of CCHF vOTU (virus ovarian tumor domain) overlaid with that the recently elucidated vOTU from the Dugbe nairovirus. This illustrates that nairovirus vOTUs have a conserved 3-D structure placing I13R and P77D in the same location throughout nairoviruses vOTUs. Similarly, FIG. 14 shows that P77D and I13R are highly conserved amongst strains of CCHFV (top) and other nairoviruses (bottom), particularly those known to cause human disease, the I13 and P77 amino acid sites are conserved.

This shows the general applicability of this invention to create recombinant forms of any one of these viruses and other homologs to have decreased deubiquitinating and decreased deISGylating activity while maintaining protease activity.

Testing and Commercial Use for Immunization and Treatment

Once a virus according to this invention has been generated and tested in tissue culture, its ability to elicit an immune response and/or prevent viral infection can be tested in a suitable animal model. Suckling mice is a suitable system to test the benefits of the vaccine. For proof of concept, a homologous nairovirus can be used. For NSDV (Nairobi Sheep Disease Virus), sheep are the ideal and easiest test model, since it is often fatal in sheep. For Erve virus, wild-type mouse models can be used. For Dugbe, Hazara, or Erve virus, suckling mice is an accepted model for the safety and efficacy of the vaccine as their immune system is immature.

In any of these models, a suitable end point would be protection, reduced fever, reduced duration of infection, or at least prolonged survival. Blood samples are taken before the testing and periodically after administration to measure antibody response, cellular response, and virus inhibition. An increase in any one or more of these responses is expected to correlate with clinical efficacy. Such experiments can be used not only to test the safety and efficacy of the vaccine in general terms, it can also be used to determine the effective dose.

In general terms, the vaccine is assembled by combining the recombinant virus in a suitable medium or vehicle in accordance with its intended route of administration. The ingredients are compounded into a medicament in accordance with generally accepted procedures for the preparation of pharmaceutical preparations, as described in standard textbooks on the subject. See, for example, Pharmaceutical Preformulation and Formulation A Practical Guide from Candidate Drug Selection to Commercial Dosage Form, M Gibson ed., Informa Health Care 2009, Pharmaceutical Manufacturing Handbook Production and Processes, S C Gad ed., Wiley-Interscience 2008, and the latest edition of Remington's Pharmaceutical Sciences, Maack Publishing Co, Easton Pa.

Steps in the compounding or formulating of the medicament depend in part on the intended use and mode of administration. Typically, the vaccine will be administered intramuscularly, subcutaneously, or orally. It can be prepared for commercial distribution with any of the following procedures in any effective combination: sterilizing, mixing with appropriate non-toxic and non-interfering excipients, buffers and other carriers, lyophilizing or freezing, dividing into dose units, and enclosing in a delivery device The medicament will typically be packaged in a suitable container accompanied by or associated with written information about its intended use, such as prophylaxis or treatment of hemorrhagic fever A suitable agent as the active ingredient is a modified virus according to this invention as a live virus type vaccine. Alternatively, after replicating in culture, the virus can be inactivated with UV irradiation or chemical means, and the viral particles used with a suitable adjuvant. In essence, attenuation of the vOTU could be used as a safeguard to prevent dangerous live wild type CCHFV from escaping physical attenuation methods for making CCHFV vaccines. The physical attenuation would prevent possible reversion of the virus.

For the purpose of prophylaxis against viral infection, if the subject is adequately primed (such as by previous immunization or infection with the target virus), a single administration of the composition may be sufficient to raise a protective immune response. Multiple administrations are more typical in an immunologically naive host. Desirable outcomes include induction or enhancement of a specific antibody response measured by a suitable test, such as enzyme-linked immunosorbent assay (ELISA) using viral antigens, or a virus neutralization assay.

For purposes of treatment or eradication of an ongoing infections disease, multiple administrations of the antigen-adjuvant composition (at least 2 or 4, for example, on a biweekly schedule) may be helpful. Here, the objective may be not just to elicit specific antibody, but also to elicit a specific T-lymphocyte response (measured in an ELISPOT™ or proliferation assay), or a cytotoxic T cell response (measurable, for example, in a cytotoxicity assay). Clinical benefit would be manifest as a reduction in the titer of virus or infectious particles in blood or in a tissue biopsy, or a limitation in the progression of necrosis, pain, wasting, or other signs of the disease.

Ultimate choice of the treatment protocol, dose, and monitoring is the responsibility of the managing clinician.
Other Genetic Alterations and Other Viruses CCHF virus and the particular mutations I13R/P77D are used throughout the disclosure for purposes of illustration, and not to limit the practice of the invention.

A person practicing the invention may, as an alternative, change I13 and/or P77 to another amino acid, and/or change other residues in the vOTU protein—so long as the resultant virus has decreased deubiquitinating activity and/or decreased deISGylating activity, and is still able to replicate in a suitable host cell.

vOTU variants with reduced enzyme activity can be generated by site-directed mutagenesis to introduce a known change into the primary structure if the wild type virus or another variant. The altered virus is then assayed for activity—namely (and in any combination), deubiquitinating activity, deISGylating activity, vOTU protease activity, ability to replicate, and/or ability to suppress cytokines such as interferon β. Thus, another amino acid can be substituted at positions I13 and/or P77, and/or at positions nearby in the tertiary structure. Possible changes include substitutions of one codon for another, and deletions or additions to the encoded amino acid sequence in any combination. Preferred changes will typically retain the tertiary structure of the wild-type virus. For the influence of vOTU structure on enzyme activity, see Capodagli, Pegan et al., J Virol. 2013; 87(7):3815-27.

vOTU variants with reduced enzyme activity can also be generated by introducing random mutations into the virus, screening colonies with a functional assay, and selecting colonies with the desired level of enzymatic activity. The particular mutation in the selected virus can then be characterized as to what changes have been made to the viral genome.

Because the genomes of nairoviruses are highly conserved, the invention can also be practiced with other strains of CCHF virus and with other nairoviruses. Possible wild-type nairoviruses that can be modified according to this invention are referred to in various places in this disclosure. Included are the following:

Nairobi Sheep Disease (NSDV; Africa) I Ganjam (Indian variant) is a fatal sheep and goat disease that particularly hinders livestock transport in Africa Dugbe virus causes mild flu-like symptoms in humans, goats, and sheep. It is present in various parts of Africa and Asia, such as Hazara, Kupe, Dera Ghazi Khan, Hughes, Qalyub, Sakhalin, and Thiafora.

FIGS. 13 and 14 show that quite a number of CCHF viral strains and other nairoviruses are conserved at amino acid positions 13 and 77. Accordingly, the same genetic alterations should have the same biological effects: reduced deubiquitinating and deISGylating activity, while still allowing the virus to replicate.

Besides site directed and random mutagenesis, vOTU variants with reduced enzyme activity can be obtained by building a hybrid virus in which the wild type glycoprotein (M segment) of a nairovirus is replaced with the M segment of another virus having the desired functionality—such as the CCHF I13R/P77D double mutant.

Directed or random changes to a nairovirus genome, and genetic alterations in nairoviruses other than CCHF virus, can be initially screened and tested for vOTU function using assays for deubiquitinating activity and/or deISGylating activity. By way of illustration, a suitable assay for deubiquitination and deISGylation activity can be run as follows. Typically, assays are performed in duplicate in 100 mM NaCl, 50 mM HEPES pH 7.5, 0.01 mg/mL bovine serum albumin (BSA), and 5 mM DTT. A suitable microtiter plate is Corning Costar™ half-volume black 96-well plate with a reaction volume of 50 μL. The reactions are observed with a matching plate reader, such as an Infinite™ M1000 series reader (Tecan, Inc.). The reaction is followed using ubiquitin or other vOTU substrate conjugated to a fluorescent tag, such as 7-amino-4-methylcourmarin (AMC). AMC becomes fluorescent (excitation λ, 360 nm; emission, 460 nm) upon decoupling from the ubiquitin or ISG15.

Suitable substrate conjugates are Ub-AMC, human ISG15-AMC (hISG15-AMC), (Boston Biochem, MA) and ZRLRGG-AMC (SEQ ID NO:22) (Bachem). ZRLRGG (SEQ ID NO:23) is a hexapeptide homologous the carboxy terminal of ubiquitin. Release of AMC is monitored by combining the substrate with wild type (WT) or mutant CCHF vOTU. The extinction coefficients for all three fluorescent substrates can be determined by adding excess vOTU to various concentrations of each substrate and allowing the reactions to run to completion. The resulting maximum fluorescence values are plotted to determine the slope and consequently each substrate's extinction coefficient. Suitable substrate concentrations to measure turnover rates in this assay are of the order of 1 μM hISG15-AMC with 20 nM vOTU; 1 μM hUb-AMC with 4 nM vOTU, and 50 μM ZRLRGG-AMC (SEQ ID NO:22) with 4 μM vOTU from either wild type or genetically altered virus.

Advantages

In summary, this invention provides a new technology to produce replicating viral particles suitable for use in a vaccine. Advantages include the following:

- CCHF virus with selective mutations can now be produced in human cell lines, avoiding xenogeneic antigen contaminants from animal tissue.
- Proven structurally biology-guided mutations of viral ovarian tumor domain proteases ablate deubiquitinating and deISGylating activity.
- The recombinant system methodology of this invention can be used to recombinantly generate any nairovirus, or CCHF virus strain. because of the homology.
- The method of genetic modification through ablation of deubiquitinating and deISGylating activity can be used in conjunction with physical attenuation methods to ensure a greater level of public safety when administering the vaccine.

SEQUENCES

```
Reverse genetics system generated Crimean-Congo hemorrhagic fever virus's L-Protein
amino acid sequence
                                                                 (SEQ. ID NO: 1)
MDFLRSLDWTQVRAGQYVSNPRFNISDYFEIVRQPGDGNCFYHSIAELTMPNKTDHSYHYIKRLTESAARKYYQEEDEARLVGL SLEDYLKRMLSDNEWGSTLEASMLAKEMGITIIIWTVAASDEVEAGIKFGDGDVFTAVNLLHSGQTHFDALRILPQFETDTREA LSLMDRVIAVDQLTSSSSDELQDYEDLALALTSAEESNRRSSLDEVTLSKKQAEILRQKASQLSKLVNKSQNIPTRVGRVLDCM FNCKLCVEISADTLILRPESKEKIGEIMSLRQLGHKLLTRDKQIKQEFSRMKLYVTKDLLDHLDVGGLLRAAFPGTGIERHMQL LHSEMILDICTVSLGVMLSTFLYGSNNKNKKKFITNCLLSTALSGKKVYKVLGNLGNELLYKAPRKALATVCSALFGKQINKLQ NCFRTISPVSLLALRNLDFDCLSVQDYNGMIENMSKLDNTDVEFNHREIADLNQLTSRLITLRKEKDTDLLKQWFPESDLTRRS IRNAANAEEFVISEFFKKKDIMKFISTSGRAMSAGKIGNVLSYAHNLYLSKSSLNMTSEDISQLLIEIKRLYALQEDSEVEPIA IICDGIESNMKQLFAILPPDCARECEVLFDDIRNSPTHSTAWKHALRLKGTAYEGLFANCYGWQYIPEDIKPSLTMLIQTLFPD KFEDFLDRTQLHPEFRDLTPDFSLTQKVHFKRNQIPSVENVQISIDATLPESVEAVPVTERKMFPLPETPLSEVHSIERIMENF TRLMHGGRLSTKKRDGDPAEQGNQQSITEHESSSISAFKDYGERGIVEENHMKFSGEDQLETRQLLLVEVGFQTDIDGKIRTDH KKWKDILKLLELLGIKCSFIACADCSSTPPDRWWITEDRVRVLKNSVSFLFNKLSRNSPTEVTDIVVGAISTQKVRSYLKAGTA TKTPVSTKDVLETWEKMKEHILNRPTGLTLPTSLEQAMRKGLVEGVVISKEGSESCINMLKENLDRITDEFERTKFKHELTQNI TTSEKMLLSWLSEDIKSSRCGECLSNIKKAVDETANLSEKIELLAYNLQLTNHCSNCHPNGVNISNTSNVCKRCPKIEVVSHCE NKGFEDSNECLTDLDRLVRLTLPGKTEKERRVKRNVEYLIKLMMSMSGIDCIKYPTGQLITHGRVSAKHNDGNLKDRSDDDQRL AEKIDTVRKELSESKLKDYSTYARGVISNSLKNLSRQGKSKCSVPRSWLEKVLFDLKVPTKDEEVLINIRNSLKARSEFVRNND KLLIRSKEELKKCFDVQSFKLKKNKQPVPFQVDCILFKEVAAECMKRYIGTPYEGIVDTLVSLINVLTRFTWFQEVVLYGKICE TFLRCCTEFNRSGVKLVKIRHCNINLSVKLPSNKKENMLCCLYSGNMELLQGPFYLNRRQAVLGSSYLYIVITLYIQVLQQYRC LEVINSVSEKTLQDIENHSMTLLEDSFREITFALEGRFEESYKIRTSRCRASGNFLNRSSRDHFISVVSGLNLVYGFLIKDNLL ANSQQQNKQLQMLRFGMLAGLSRLVCPNELGKKFSTSCRRIEDNIARLYLQTSIYCSVRDVEDNVKHWKQRDLCPEVTIPCFTV YGTFVNSDRQLIFDIYNVHIYNKEMDNFDEGCISVLEETAERHMLWELDLMNSLCSDEKKDTRTARLLLGCPNVRKAANREGKK LLKLNSDTSTDTQSIASEVSDRRSYSSSKSRIRSIFGRYNSQKKPFELRSGLEVFNDPFNDYQQAITDICQFSEYTPNKESILK DCLQIIRKNPSHTMGSFELIQAISEFGMSKFPPENIDKARRDPKNWVSISEVTETTSIVASPRTHMMLKDCFKIILGTENKKIV KMLRGKLKKLGAISTNIEIGKRDCLDLLSTVDGLTDQQKENIVNGIFEPSKLSFYHWKELVKKNIDEVLLTEDGNLIFCWLKTI SSSVKGSLKKRLKFMNIHSPELMPENCLFSSEEFNELIKLKKLLLNEQQDEQELKQDLLISSWIKCITACKDFASINDKIQKFI YHLSEELYDIRLQHLELSKLKQEHPSVSFTKEEVLIKRLEKNFLKQHNLEIMETVNLVFFAALSAPWCLHYKALESYLVRHPEI
```

-continued

LDCGSKEDCKLTLLDLSVSKLLVCLYQKDDEELINSSSLKLGFLVKYVVTLFTSNGEPFSLSLNDGGLDLDLHKTTDEKLLHQT

KIVFAKIGLSGNSYDFIWTTQMIANSNFNVCKRLTGRSTGERLPRSVRSKVIYEMVKLVGETGMAILQQLAFAQALNYEHRFYA

VLAPKAQLGGARDLLVQETGTKVMHATTEMFSRNLLKTTSDDGLTNPHLKETILNVGLDCLANMRNLDGKPISEGSNLVNFYKV

ICISGDNTKWGPIHCCSFFSGMMQQVLKNVPDWCSFYKLTFIKNLCRQVEIPAGSIKKILNVLRYRLCSKGGVEQHSEEDLRRL

LTDNLDSWDGNDTVKFLVTTYISKGLMALNSYNHMGQGIHHATSSVLTSLAAVLFEELAIFYLKRSLPQTTVHVEHAGSSDDYA

KCIVVTGILSKELYSQYDETFWKHACRLKNFTAAVQRCCQMKDSAKTLVSDCFLEFYSEFMMGYRVTPAVIKFMFTGLINSSVT

SPQSLMQACQVSSQQAMYNSVPLVTNTAFTLLRQQIFFNHVEDFIRRYGILTLGTLSPFGRLFVPTYSGLASSTVALEDAEVIA

RAAQTLQMNSVSIQSSSLTTLDSLGRSRTSSTAEDSSSVSDTTAASHDSGSSSSSFSFELNRPLSETELQFIKALSSLKSTQAC

EVIQNRITGLYCNSNEGPLDRHNVIYSSRMADSCDWLKDGKRRGNLELANRIQSVLCILIAGYYRSFGGEGTEKQVKASLNRDD

NKIIEDPMIQLIPEKLRRELERLGVSRMEVDELMPSISPDDTLAQLVAKKLISLNVSTEEYSAEVSRLKQTLTARNVLHGLAGG

IKELSLPIYTIFMKSYFFKDNVFLSLTDRWSTKHSTNYRDSCGKQLKGRIITKYTHWLDTFLGCSVSINRHTTVKEPSLFNPNI

RCVNLITFEDGLRELSVIQSHLKVFENEFTNLNLQFSDPNRQKLRIVESRPAESELEANRAVIVKTKLFSATEQVRLSNNPAVV

MGYLLDESAISEVKPTKVDFSNLLKDRFKIMQFFPSVFTLIKMLTDESSDSEKSGLSPDLQQVARYSNHLTLLSRMIQQAKPTV

TVFYMLKGNLMNTEPTVAELVSYGIKEGRFFRLSDTGVDASTYSVKYWKILHCISAIGCLPLSQADKSSLLMSFLNWRVNMDIR

TSDCPLSSHEASILSEFDGQVIANILASELSSVKRDSEREGLTDLLDYLNSPTELLKKKPYLGTTCKFNTWGDSNRSGKFTYSS

RSGESIGIFIAGKLHIHLSSESVALLCETERQVLSWMSKRRTEVITKEQHQLFLSLLPQSHECLQKHKDGSALSVIPDSSNPRL

LKFVPLKKGLAVVKIKKQILTVKKQVVFDAESEPRLQWGHGCLSIVYDETDTQTTYHENLLKVKHLVDCSTDRKKLLPQSVFSD

SKVVLSRIKFKTELLLNSLTLLHCFLKHAPSDAIMEVESKSSLLHKYLKSGGVRQRNTEVLFREKLNKVVIKDNLEQGVEEEIE

FCNNLTKTVSENPLPLSCWSEVQNYIEDIGFNNVLVNIDRNTVKSELLWKFTLDTNVSTTSTIKDVRTLVSYVSTETIPKFLLA

FLLYEEVLMNLINQCKAVKELINSTGLSDLELESLLTLCAFYFQSECSKRDGPRCSFAALLSLIHEDWQRIGKNILVRANNELG

DVSLKVNIVLVPLKDMSKPKSERVVMARRSLNHALSLMFLDEMSLPELKSLSVNCKMGNFEGQECFEFTILKDNSARLDYNKLI

DHCVDMEKKREAVRAVEDLILMLTGRAVKPSAVTQFVHGDEQCQEQISLDDLMANDTVTDFPDREAEALKTGNLGFNWDSD

Reverse genetics system generated Crimean-Congo hemorrhagic fever virus's M-Protein amino acid sequence (SEQ. ID NO: 2)

MHISLMYAILCLQLCGLGETHGSHNETRHNKTDTMTTPGDNPSSEPPVSTALSITLDPSTVTPTTPASGLEGSGEVYTSPPITT

GSLPLSETTPELPVTTGTDTLSAGDVDPSTQTAGGTSAPTVRTSLPNSPSTPSTPQDTHHPVRNLLSVTSPGPDETSTPSGTGK

ESSATSSPHPVSNRPPTPPATAQGPTENDSHNATEHPESLTQSATPGLMTSPTQIVHPQSATPITVQDTHPSPTNRSKRNLKME

IILTLSQGLKKYYGKILRLLQLTEEDTEGLLEWCKRNLGLDCDDTFFQKRIEEFFITGEGHFNEVLQFRTPGTLSTTESTPAG

LPTAEPFKSYFAKGFLSIDSGYYSAKCYSGTSNSGLQLINITRHSTRIVDTPGPKITNLKTINCINLKASIFKEHREVEINVLL

PQVAVNLSNCHVVIKSHVCDYSLDIDGAVRLPHIYHEGVFIPGTYKIVIDKKNKLNDRCTLFTDCVIKGREVRKGQSVLRQYKT

EIRIGKASTGSRRLLSEEPSDDCISRTQLLRTETAEIHGDNYGGPGDKITICNGSTIVDQRLGSELGCYTINRVRSFKLCENSA

TGKNCEIDSVPVKCRQGYCLRITQEGRGHVKLSRGSEVVLDACDTSCEIMIPKGTGDILVDCSGGQQHFLKDNLIDLGCPKIPL

LGKMAIYICRMSNHPKTTMAFLFWFSFGYVITCILCKAIFYLLIIVGTLGKRLKQYRELKPQTCTICETTPVNAIDAEMHDLNC

SYNICPYCASRLTSDGLARHVIQCPKRKEKVEETELYLNLERIPWVVRKLLQVSESTGVALKRSSWLIVLLVLFTVSLSPVQSA

PIGQGKTIEAYRAREGYTSICLFVLGSILFIVSCLMKGLVDSVGNSFFPGLSICKTCSISSINGFEIESHKCYCSLFCCPYCRH

CSTDKEIHKLHLSICKKRKKGSNVMLAVCKLMCFRATMEVSNRALFIRSIINTTFVLCILILAVCVVSTSAVEMENLPAGTWER

EEDLTNFCHQECQVTETECLCPYEALVLRKPLFLDSTAKGMKNLLNSTSLETSLSIEAPWGAINVQSTYKPTVSTANIALSWSS

VEHRGNKILVSGRSESIMKLEERTGISWDLGVEDASESKLLTVSVMDLSQMYSPVFEYLSGDRQVGEWPKATCTGDCPERCGCT

SSTCLHKEWPHSRNWRCNPTWCWGVGTGCTCCGLDVKDLFTDYMFVKWKVEYIKTEAIVCVELTSQERQCSLIEAGTRFNLGPV

TITLSEPRNIQQKLPPEIITLHPRIEEGFFDLMHVQKVLSASTVCKLQSCTHGVPGDLQVYHIGNLLKGDKVNGHLIHKIEPHF

NTSWMSWDGCDLDYYCNMGDWPSCTYTGVTQHNHASFVNLLNIETDYTKNFHFHSKRVTAHGDTPQLDLKARPTYGAGEITVLV

-continued

EVADMELHTKKIEISGLKFASLACTGCYACSSGISCKVRIHVDEPDELTVHVKSDDPDVVAASSSLMARKLEFGTDSTFKAFSA

MPKTSLCFYIVEREHCKSCSEEDTKKCVNTKLEQPQSILIEHKGTIIGKQNSTCTAKASCWLESVKSFFYGLKNMLSGIFGNVF

MGIFLFLAPFILLILFFMFGWRILFCFKCCRRTRGLFKYRHLKDDEETGYRRIIEKLNNKKGKNKLLDGERLADRRIAELFSTK

THIG

Reverse genetics system generated Crimean-Congo hemorrhagic fever virus's S-Protein amino acid sequence (SEQ. ID NO: 3)

MENKIEVNNKDEMNRWFEEFKKGNGLVDTFTNSYSFCESVPNLDRFVFQMASATDDAQKDSIYASALVEATKFCAPIYECAWVS

STGIVKKGLEWFEKNAGTIKSWDESYTELKVDVPKIEQLTGYQQAALKWRKDIGFRVNANTAALSNKVLAEYKVPGEIVMSVKE

MLSDMIRRRNLILNRGGDENPRGPVSHEHVDWCREFVKGKYIMAFNPPWGDINKSGRSGIALVATGLAKLAETEGKGIFDEAKK

TVEALNGYLDKHKDEVDRASADSMITNLLKHIAKAQELYKNSSALRAQSAQIDTAFSSYYWLYKAGVTPETFPTVSQFLFELGK

QPRGTKKMKKALLSTPMKWGKKLYELFADDSFQQNRIYMHPAVLTAGRISEMGVCFGTIPVANPDDAAQGSGHTKSILNLRTNT

ETNNPCAKTIVKLFEVQKTGFNIQDMDIVASEHLLHQSLVGKQSPFQNAYNVKGNATSANII

For all purposes in the United States of America, each and every publication and patent document cited herein is incorporated herein by reference as if each such publication or document was specifically and individually indicated to be incorporated herein by reference.

While the invention has been described with reference to the specific embodiments, changes can be made and equivalents can be substituted to adapt to a particular context or intended use, thereby achieving benefits of the invention without departing from the scope of what is claimed.

The invention claimed is:

1. A pharmaceutical composition effective in eliciting a specific immune response, comprising a recombinantly altered Crimean-Congo hemorrhagic fever (CCHF) virus comprising an L protein that has been recombinantly altered to have decreased deubiquitinating activity or decreased deISGylating activity while maintaining protease activity, such that the CCHF virus replicates in human cells, wherein the recombinantly altered L protein is altered at a position corresponding to a ubiquitin or ISG15 substrate binding interface of OTU domain protease.

2. The immunogenic composition of claim 1, which has been recombinantly altered to have both decreased deubiquitinating activity and decreased deISGylating activity.

3. The immunogenic composition of claim 1, wherein the virus has been chemically or radiologically inactivated.

4. The immunogenic composition of claim 1, which has been modified wherein the L protein comprises a substitution at position 13, position 77, or both position 13 and 77 of the L protein.

5. The immunogenic composition of claim 4, wherein position 13 of the L protein is changed to arginine.

6. The immunogenic composition of claim 4, wherein position 77 of the L protein is changed to aspartic acid.

7. The immunogenic composition of claim 1, further comprising an adjuvant.

8. A recombinantly altered CCHF virus comprising an L protein that has been recombinantly altered to have both decreased deubiquitinating activity and decreased deISGylating activity while maintaining protease activity, such that the CCHF virus replicates in human cells, wherein the recombinantly altered L protein is altered at a position corresponding to a ubiquitin or ISG15 substrate binding interface of OTU domain protease.

9. The recombinantly altered virus of claim 8, which has been modified wherein the L protein comprises a substitution at position 13, position 77, or both position 13 and 77 of the L protein.

10. The recombinantly altered virus of claim 8, wherein position 13 of the L protein is changed to arginine.

11. The recombinantly altered virus of claim 8, wherein position 77 of the L protein is changed to aspartic acid.

12. The recombinantly altered virus of claim 8, wherein the virus has no ability or a reduced ability to inhibit expression of interferon β.

13. A host human cell line transfected with a recombinantly altered virus according to claim 8.

14. A method of eliciting an immune response against a recombinantly altered CCHF virus, comprising administering to a subject in need thereof an immunogenic composition according to claim 1.

15. A method of developing an immunogenic but substantially non-pathogenic CCHF virus, comprising:
   a) transfecting a host cell with the genome of a recombinantly altered CCHF virus;
   b) transfecting the host cell with a codon optimized L protein expression vector and an N protein expression vector;
   c) obtaining replicated virus particles comprising said genetic alterations from the host cell; and
   d) testing the replicated virus particles for decreased deubiquitinating activity and/or decreased deISGylating activity; and
   e) selecting one or more virus particles with decreased deubiquitinating activity and/or decreased deISGylating activity.

16. The method of claim 15, wherein step (a) comprises transfecting the host cell with the L, M, and S gene sectors in separate vectors.

17. A method for preparing a commercial product, comprising packaging a pharmaceutical composition according to claim 1 with information on how to use the product for eliciting an immune response against a CCHF virus.

* * * * *

SEQUENCE LISTING

```
<160> NUMBER OF SEQ ID NOS: 23

<210> SEQ ID NO 1
<211> LENGTH: 3945
<212> TYPE: PRT
<213> ORGANISM: Artificial Sequence
<220> FEATURE:
<223> OTHER INFORMATION: synthetic Nairovirus Crimean-Congo hemorrhagic
      fever virus (CCHFV) modified L (Large) protein I13R/P77D double
      mutation reducing deubiquinating and deISGylating activities, RNA
      polymerase and viral ovarian tumor domain protease (vOTU)
<220> FEATURE:
<221> NAME/KEY: DOMAIN
<222> LOCATION: (1)...(169)
<223> OTHER INFORMATION: viral ovarian tumor domain protease (vOTU)

<400> SEQUENCE: 1

Met Asp Phe Leu Arg Ser Leu Asp Trp Thr Gln Val Arg Ala Gly Gln
  1               5                  10                  15

Tyr Val Ser Asn Pro Arg Phe Asn Ile Ser Asp Tyr Phe Glu Ile Val
                 20                  25                  30

Arg Gln Pro Gly Asp Gly Asn Cys Phe Tyr His Ser Ile Ala Glu Leu
             35                  40                  45

Thr Met Pro Asn Lys Thr Asp His Ser Tyr His Tyr Ile Lys Arg Leu
         50                  55                  60

Thr Glu Ser Ala Ala Arg Lys Tyr Tyr Gln Glu Asp Glu Ala Arg
 65                  70                  75                  80

Leu Val Gly Leu Ser Leu Glu Asp Tyr Leu Lys Arg Met Leu Ser Asp
                 85                  90                  95

Asn Glu Trp Gly Ser Thr Leu Glu Ala Ser Met Leu Ala Lys Glu Met
                100                 105                 110

Gly Ile Thr Ile Ile Ile Trp Thr Val Ala Ala Ser Asp Glu Val Glu
            115                 120                 125

Ala Gly Ile Lys Phe Gly Asp Gly Asp Val Phe Thr Ala Val Asn Leu
        130                 135                 140

Leu His Ser Gly Gln Thr His Phe Asp Ala Leu Arg Ile Leu Pro Gln
```

```
                145                 150                 155                 160
        Phe Glu Thr Asp Thr Arg Glu Ala Leu Ser Leu Met Asp Arg Val Ile
                        165                 170                 175
        Ala Val Asp Gln Leu Thr Ser Ser Ser Asp Glu Leu Gln Asp Tyr
                        180                 185                 190
        Glu Asp Leu Ala Leu Ala Leu Thr Ser Ala Glu Glu Ser Asn Arg Arg
                        195                 200                 205
        Ser Ser Leu Asp Glu Val Thr Leu Ser Lys Lys Gln Ala Glu Ile Leu
                210                 215                 220
        Arg Gln Lys Ala Ser Gln Leu Ser Lys Leu Val Asn Lys Ser Gln Asn
        225                 230                 235                 240
        Ile Pro Thr Arg Val Gly Arg Val Leu Asp Cys Met Phe Asn Cys Lys
                        245                 250                 255
        Leu Cys Val Glu Ile Ser Ala Asp Thr Leu Ile Leu Arg Pro Glu Ser
                        260                 265                 270
        Lys Glu Lys Ile Gly Glu Ile Met Ser Leu Arg Gln Leu Gly His Lys
                        275                 280                 285
        Leu Leu Thr Arg Asp Lys Gln Ile Lys Gln Glu Phe Ser Arg Met Lys
                        290                 295                 300
        Leu Tyr Val Thr Lys Asp Leu Leu Asp His Leu Asp Val Gly Gly Leu
        305                 310                 315                 320
        Leu Arg Ala Ala Phe Pro Gly Thr Gly Ile Glu Arg His Met Gln Leu
                        325                 330                 335
        Leu His Ser Glu Met Ile Leu Asp Ile Cys Thr Val Ser Leu Gly Val
                        340                 345                 350
        Met Leu Ser Thr Phe Leu Tyr Gly Ser Asn Asn Lys Asn Lys Lys Lys
                        355                 360                 365
        Phe Ile Thr Asn Cys Leu Leu Ser Thr Ala Leu Ser Gly Lys Lys Val
                        370                 375                 380
        Tyr Lys Val Leu Gly Asn Leu Gly Asn Glu Leu Leu Tyr Lys Ala Pro
        385                 390                 395                 400
        Arg Lys Ala Leu Ala Thr Val Cys Ser Ala Leu Phe Gly Lys Gln Ile
                        405                 410                 415
        Asn Lys Leu Gln Asn Cys Phe Arg Thr Ile Ser Pro Val Ser Leu Leu
                        420                 425                 430
        Ala Leu Arg Asn Leu Asp Phe Asp Cys Leu Ser Val Gln Asp Tyr Asn
                        435                 440                 445
        Gly Met Ile Glu Asn Met Ser Lys Leu Asp Asn Thr Asp Val Glu Phe
                        450                 455                 460
        Asn His Arg Glu Ile Ala Asp Leu Asn Gln Leu Thr Ser Arg Leu Ile
        465                 470                 475                 480
        Thr Leu Arg Lys Glu Lys Asp Thr Asp Leu Lys Gln Trp Phe Pro
                        485                 490                 495
        Glu Ser Asp Leu Thr Arg Arg Ser Ile Arg Asn Ala Ala Asn Ala Glu
                        500                 505                 510
        Glu Phe Val Ile Ser Glu Phe Phe Lys Lys Asp Ile Met Lys Phe
                        515                 520                 525
        Ile Ser Thr Ser Gly Arg Ala Met Ser Ala Gly Lys Ile Gly Asn Val
                        530                 535                 540
        Leu Ser Tyr Ala His Asn Leu Tyr Leu Ser Lys Ser Ser Leu Asn Met
        545                 550                 555                 560
        Thr Ser Glu Asp Ile Ser Gln Leu Leu Ile Glu Ile Lys Arg Leu Tyr
                        565                 570                 575
```

```
Ala Leu Gln Glu Asp Ser Glu Val Glu Pro Ile Ala Ile Ile Cys Asp
            580                 585                 590
Gly Ile Glu Ser Asn Met Lys Gln Leu Phe Ala Ile Leu Pro Pro Asp
        595                 600                 605
Cys Ala Arg Glu Cys Glu Val Leu Phe Asp Asp Ile Arg Asn Ser Pro
    610                 615                 620
Thr His Ser Thr Ala Trp Lys His Ala Leu Arg Leu Lys Gly Thr Ala
625                 630                 635                 640
Tyr Glu Gly Leu Phe Ala Asn Cys Tyr Gly Trp Gln Tyr Ile Pro Glu
                645                 650                 655
Asp Ile Lys Pro Ser Leu Thr Met Leu Ile Gln Thr Leu Phe Pro Asp
            660                 665                 670
Lys Phe Glu Asp Phe Leu Asp Arg Thr Gln Leu His Pro Glu Phe Arg
        675                 680                 685
Asp Leu Thr Pro Asp Phe Ser Leu Thr Gln Lys Val His Phe Lys Arg
    690                 695                 700
Asn Gln Ile Pro Ser Val Glu Asn Val Gln Ile Ser Ile Asp Ala Thr
705                 710                 715                 720
Leu Pro Glu Ser Val Glu Ala Val Pro Val Thr Glu Arg Lys Met Phe
                725                 730                 735
Pro Leu Pro Glu Thr Pro Leu Ser Glu Val His Ser Ile Glu Arg Ile
            740                 745                 750
Met Glu Asn Phe Thr Arg Leu Met His Gly Gly Arg Leu Ser Thr Lys
        755                 760                 765
Lys Arg Asp Gly Asp Pro Ala Glu Gln Gly Asn Gln Gln Ser Ile Thr
    770                 775                 780
Glu His Glu Ser Ser Ser Ile Ser Ala Phe Lys Asp Tyr Gly Glu Arg
785                 790                 795                 800
Gly Ile Val Glu Glu Asn His Met Lys Phe Ser Gly Glu Asp Gln Leu
                805                 810                 815
Glu Thr Arg Gln Leu Leu Val Glu Val Gly Phe Gln Thr Asp Ile
            820                 825                 830
Asp Gly Lys Ile Arg Thr Asp His Lys Lys Trp Lys Asp Ile Leu Lys
    835                 840                 845
Leu Leu Glu Leu Leu Gly Ile Lys Cys Ser Phe Ile Ala Cys Ala Asp
850                 855                 860
Cys Ser Ser Thr Pro Pro Asp Arg Trp Trp Ile Thr Glu Asp Arg Val
865                 870                 875                 880
Arg Val Leu Lys Asn Ser Val Ser Phe Leu Phe Asn Lys Leu Ser Arg
                885                 890                 895
Asn Ser Pro Thr Glu Val Thr Asp Ile Val Val Gly Ala Ile Ser Thr
            900                 905                 910
Gln Lys Val Arg Ser Tyr Leu Lys Ala Gly Thr Ala Thr Lys Thr Pro
        915                 920                 925
Val Ser Thr Lys Asp Val Leu Glu Thr Trp Glu Lys Met Lys Glu His
    930                 935                 940
Ile Leu Asn Arg Pro Thr Gly Leu Thr Leu Pro Thr Ser Leu Glu Gln
945                 950                 955                 960
Ala Met Arg Lys Gly Leu Val Glu Gly Val Val Ile Ser Lys Glu Gly
                965                 970                 975
Ser Glu Ser Cys Ile Asn Met Leu Lys Glu Asn Leu Asp Arg Ile Thr
            980                 985                 990
```

-continued

```
Asp Glu Phe Glu Arg Thr Lys Phe Lys His Glu Leu Thr Gln Asn Ile
            995                 1000                1005

Thr Thr Ser Glu Lys Met Leu Leu Ser Trp Leu Ser Glu Asp Ile Lys
        1010                1015                1020

Ser Ser Arg Cys Gly Glu Cys Leu Ser Asn Ile Lys Lys Ala Val Asp
1025                1030                1035                1040

Glu Thr Ala Asn Leu Ser Glu Lys Ile Glu Leu Leu Ala Tyr Asn Leu
            1045                1050                1055

Gln Leu Thr Asn His Cys Ser Asn Cys His Pro Asn Gly Val Asn Ile
        1060                1065                1070

Ser Asn Thr Ser Asn Val Cys Lys Arg Cys Pro Lys Ile Glu Val Val
            1075                1080                1085

Ser His Cys Glu Asn Lys Gly Phe Glu Asp Ser Asn Glu Cys Leu Thr
        1090                1095                1100

Asp Leu Asp Arg Leu Val Arg Leu Thr Leu Pro Gly Lys Thr Glu Lys
1105                1110                1115                1120

Glu Arg Arg Val Lys Arg Asn Val Glu Tyr Leu Ile Lys Leu Met Met
            1125                1130                1135

Ser Met Ser Gly Ile Asp Cys Ile Lys Tyr Pro Thr Gly Gln Leu Ile
        1140                1145                1150

Thr His Gly Arg Val Ser Ala Lys His Asn Asp Gly Asn Leu Lys Asp
        1155                1160                1165

Arg Ser Asp Asp Asp Gln Arg Leu Ala Glu Lys Ile Asp Thr Val Arg
    1170                1175                1180

Lys Glu Leu Ser Glu Ser Lys Leu Lys Asp Tyr Ser Thr Tyr Ala Arg
1185                1190                1195                1200

Gly Val Ile Ser Asn Ser Leu Lys Asn Leu Ser Arg Gln Gly Lys Ser
            1205                1210                1215

Lys Cys Ser Val Pro Arg Ser Trp Leu Glu Lys Val Leu Phe Asp Leu
        1220                1225                1230

Lys Val Pro Thr Lys Asp Glu Val Leu Ile Asn Ile Arg Asn Ser
        1235                1240                1245

Leu Lys Ala Arg Ser Glu Phe Val Arg Asn Asn Asp Lys Leu Leu Ile
        1250                1255                1260

Arg Ser Lys Glu Glu Leu Lys Lys Cys Phe Asp Val Gln Ser Phe Lys
1265                1270                1275                1280

Leu Lys Lys Asn Lys Gln Pro Val Pro Phe Gln Val Asp Cys Ile Leu
            1285                1290                1295

Phe Lys Glu Val Ala Ala Glu Cys Met Lys Arg Tyr Ile Gly Thr Pro
            1300                1305                1310

Tyr Glu Gly Ile Val Asp Thr Leu Val Ser Leu Ile Asn Val Leu Thr
        1315                1320                1325

Arg Phe Thr Trp Phe Gln Glu Val Val Leu Tyr Gly Lys Ile Cys Glu
    1330                1335                1340

Thr Phe Leu Arg Cys Cys Thr Glu Phe Asn Arg Ser Gly Val Lys Leu
1345                1350                1355                1360

Val Lys Ile Arg His Cys Asn Ile Asn Leu Ser Val Lys Leu Pro Ser
        1365                1370                1375

Asn Lys Lys Glu Asn Met Leu Cys Cys Leu Tyr Ser Gly Asn Met Glu
        1380                1385                1390

Leu Leu Gln Gly Pro Phe Tyr Leu Asn Arg Arg Gln Ala Val Leu Gly
        1395                1400                1405

Ser Ser Tyr Leu Tyr Ile Val Ile Thr Leu Tyr Ile Gln Val Leu Gln
```

```
               1410                1415                1420
Gln Tyr Arg Cys Leu Glu Val Ile Asn Ser Val Ser Glu Lys Thr Leu
1425                1430                1435                1440

Gln Asp Ile Glu Asn His Ser Met Thr Leu Leu Glu Asp Ser Phe Arg
                1445                1450                1455

Glu Ile Thr Phe Ala Leu Glu Gly Arg Phe Glu Ser Tyr Lys Ile
                1460                1465                1470

Arg Thr Ser Arg Cys Arg Ala Ser Gly Asn Phe Leu Asn Arg Ser Ser
                1475                1480                1485

Arg Asp His Phe Ile Ser Val Val Ser Gly Leu Asn Leu Val Tyr Gly
                1490                1495                1500

Phe Leu Ile Lys Asp Asn Leu Leu Ala Asn Ser Gln Gln Gln Asn Lys
1505                1510                1515                1520

Gln Leu Gln Met Leu Arg Phe Gly Met Leu Ala Gly Leu Ser Arg Leu
                1525                1530                1535

Val Cys Pro Asn Glu Leu Gly Lys Lys Phe Ser Thr Ser Cys Arg Arg
                1540                1545                1550

Ile Glu Asp Asn Ile Ala Arg Leu Tyr Leu Gln Thr Ser Ile Tyr Cys
                1555                1560                1565

Ser Val Arg Asp Val Glu Asp Asn Val Lys His Trp Lys Gln Arg Asp
                1570                1575                1580

Leu Cys Pro Glu Val Thr Ile Pro Cys Phe Thr Val Tyr Gly Thr Phe
1585                1590                1595                1600

Val Asn Ser Asp Arg Gln Leu Ile Phe Asp Ile Tyr Asn Val His Ile
                1605                1610                1615

Tyr Asn Lys Glu Met Asp Asn Phe Asp Glu Gly Cys Ile Ser Val Leu
                1620                1625                1630

Glu Glu Thr Ala Glu Arg His Met Leu Trp Gly Leu Asp Leu Met Asn
                1635                1640                1645

Ser Leu Cys Ser Asp Glu Lys Lys Asp Thr Arg Thr Ala Arg Leu Leu
                1650                1655                1660

Leu Gly Cys Pro Asn Val Arg Lys Ala Ala Asn Arg Glu Gly Lys Lys
1665                1670                1675                1680

Leu Leu Lys Leu Asn Ser Asp Thr Ser Thr Asp Thr Gln Ser Ile Ala
                1685                1690                1695

Ser Glu Val Ser Asp Arg Arg Ser Tyr Ser Ser Ser Lys Ser Arg Ile
                1700                1705                1710

Arg Ser Ile Phe Gly Arg Tyr Asn Ser Gln Lys Lys Pro Phe Glu Leu
                1715                1720                1725

Arg Ser Gly Leu Glu Val Phe Asn Asp Pro Phe Asn Asp Tyr Gln Gln
                1730                1735                1740

Ala Ile Thr Asp Ile Cys Gln Phe Ser Glu Tyr Thr Pro Asn Lys Glu
1745                1750                1755                1760

Ser Ile Leu Lys Asp Cys Leu Gln Ile Ile Arg Lys Asn Pro Ser His
                1765                1770                1775

Thr Met Gly Ser Phe Glu Leu Ile Gln Ala Ile Ser Glu Phe Gly Met
                1780                1785                1790

Ser Lys Phe Pro Pro Glu Asn Ile Asp Lys Ala Arg Arg Asp Pro Lys
                1795                1800                1805

Asn Trp Val Ser Ile Ser Glu Val Thr Glu Thr Thr Ser Ile Val Ala
                1810                1815                1820

Ser Pro Arg Thr His Met Met Leu Lys Asp Cys Phe Lys Ile Ile Leu
1825                1830                1835                1840
```

```
Gly Thr Glu Asn Lys Lys Ile Val Lys Met Leu Arg Gly Lys Leu Lys
            1845                1850                1855
Lys Leu Gly Ala Ile Ser Thr Asn Ile Glu Ile Gly Lys Arg Asp Cys
            1860                1865                1870
Leu Asp Leu Leu Ser Thr Val Asp Gly Leu Thr Asp Gln Gln Lys Glu
            1875                1880                1885
Asn Ile Val Asn Gly Ile Phe Glu Pro Ser Lys Leu Ser Phe Tyr His
            1890                1895                1900
Trp Lys Glu Leu Val Lys Lys Asn Ile Asp Glu Val Leu Leu Thr Glu
1905                1910                1915                1920
Asp Gly Asn Leu Ile Phe Cys Trp Leu Lys Thr Ile Ser Ser Ser Val
            1925                1930                1935
Lys Gly Ser Leu Lys Lys Arg Leu Lys Phe Met Asn Ile His Ser Pro
            1940                1945                1950
Glu Leu Met Pro Glu Asn Cys Leu Phe Ser Ser Glu Glu Phe Asn Glu
            1955                1960                1965
Leu Ile Lys Leu Lys Lys Leu Leu Asn Glu Gln Gln Asp Glu Gln
            1970                1975                1980
Glu Leu Lys Gln Asp Leu Leu Ile Ser Ser Trp Ile Lys Cys Ile Thr
1985                1990                1995                2000
Ala Cys Lys Asp Phe Ala Ser Ile Asn Asp Lys Ile Gln Lys Phe Ile
            2005                2010                2015
Tyr His Leu Ser Glu Glu Leu Tyr Asp Ile Arg Leu Gln His Leu Glu
            2020                2025                2030
Leu Ser Lys Leu Lys Gln Glu His Pro Ser Val Ser Phe Thr Lys Glu
            2035                2040                2045
Glu Val Leu Ile Lys Arg Leu Glu Lys Asn Phe Leu Lys Gln His Asn
            2050                2055                2060
Leu Glu Ile Met Glu Thr Val Asn Leu Val Phe Phe Ala Ala Leu Ser
2065                2070                2075                2080
Ala Pro Trp Cys Leu His Tyr Lys Ala Leu Glu Ser Tyr Leu Val Arg
            2085                2090                2095
His Pro Glu Ile Leu Asp Cys Gly Ser Lys Glu Asp Cys Lys Leu Thr
            2100                2105                2110
Leu Leu Asp Leu Ser Val Ser Lys Leu Leu Val Cys Leu Tyr Gln Lys
            2115                2120                2125
Asp Asp Glu Glu Leu Ile Asn Ser Ser Ser Leu Lys Leu Gly Phe Leu
            2130                2135                2140
Val Lys Tyr Val Val Thr Leu Phe Ser Asn Gly Glu Pro Phe Ser
 2145                2150                2155                2160
Leu Ser Leu Asn Asp Gly Gly Leu Asp Leu Asp Leu His Lys Thr Thr
            2165                2170                2175
Asp Glu Lys Leu Leu His Gln Thr Lys Ile Val Phe Ala Lys Ile Gly
            2180                2185                2190
Leu Ser Gly Asn Ser Tyr Asp Phe Ile Trp Thr Thr Gln Met Ile Ala
            2195                2200                2205
Asn Ser Asn Phe Asn Val Cys Lys Arg Leu Thr Gly Arg Ser Thr Gly
            2210                2215                2220
Glu Arg Leu Pro Arg Ser Val Arg Ser Lys Val Ile Tyr Glu Met Val
2225                2230                2235                2240
Lys Leu Val Gly Glu Thr Gly Met Ala Ile Leu Gln Gln Leu Ala Phe
            2245                2250                2255
```

-continued

```
Ala Gln Ala Leu Asn Tyr Glu His Arg Phe Tyr Ala Val Leu Ala Pro
            2260                2265                2270

Lys Ala Gln Leu Gly Gly Ala Arg Asp Leu Leu Val Gln Glu Thr Gly
        2275                2280                2285

Thr Lys Val Met His Ala Thr Thr Glu Met Phe Ser Arg Asn Leu Leu
    2290                2295                2300

Lys Thr Thr Ser Asp Asp Gly Leu Thr Asn Pro His Leu Lys Glu Thr
2305                2310                2315                2320

Ile Leu Asn Val Gly Leu Asp Cys Leu Ala Asn Met Arg Asn Leu Asp
            2325                2330                2335

Gly Lys Pro Ile Ser Glu Gly Ser Asn Leu Val Asn Phe Tyr Lys Val
        2340                2345                2350

Ile Cys Ile Ser Gly Asp Asn Thr Lys Trp Gly Pro Ile His Cys Cys
    2355                2360                2365

Ser Phe Phe Ser Gly Met Met Gln Gln Val Leu Lys Asn Val Pro Asp
        2370                2375                2380

Trp Cys Ser Phe Tyr Lys Leu Thr Phe Ile Lys Asn Leu Cys Arg Gln
2385                2390                2395                2400

Val Glu Ile Pro Ala Gly Ser Ile Lys Lys Ile Leu Asn Val Leu Arg
            2405                2410                2415

Tyr Arg Leu Cys Ser Lys Gly Val Glu Gln His Ser Glu Glu Asp
        2420                2425                2430

Leu Arg Arg Leu Leu Thr Asp Asn Leu Asp Ser Trp Asp Gly Asn Asp
    2435                2440                2445

Thr Val Lys Phe Leu Val Thr Thr Tyr Ile Ser Lys Gly Leu Met Ala
2450                2455                2460

Leu Asn Ser Tyr Asn His Met Gly Gln Gly Ile His His Ala Thr Ser
2465                2470                2475                2480

Ser Val Leu Thr Ser Leu Ala Ala Val Leu Phe Glu Glu Leu Ala Ile
            2485                2490                2495

Phe Tyr Leu Lys Arg Ser Leu Pro Gln Thr Thr Val His Val Glu His
        2500                2505                2510

Ala Gly Ser Ser Asp Asp Tyr Ala Lys Cys Ile Val Val Thr Gly Ile
    2515                2520                2525

Leu Ser Lys Glu Leu Tyr Ser Gln Tyr Asp Glu Thr Phe Trp Lys His
    2530                2535                2540

Ala Cys Arg Leu Lys Asn Phe Thr Ala Ala Val Gln Arg Cys Cys Gln
2545                2550                2555                2560

Met Lys Asp Ser Ala Lys Thr Leu Val Ser Asp Cys Phe Leu Glu Phe
            2565                2570                2575

Tyr Ser Glu Phe Met Met Gly Tyr Arg Val Thr Pro Ala Val Ile Lys
        2580                2585                2590

Phe Met Phe Thr Gly Leu Ile Asn Ser Ser Val Thr Ser Pro Gln Ser
    2595                2600                2605

Leu Met Gln Ala Cys Gln Val Ser Ser Gln Ala Met Tyr Asn Ser
        2610                2615                2620

Val Pro Leu Val Thr Asn Thr Ala Phe Thr Leu Leu Arg Gln Gln Ile
2625                2630                2635                2640

Phe Phe Asn His Val Glu Asp Phe Ile Arg Arg Tyr Gly Ile Leu Thr
            2645                2650                2655

Leu Gly Thr Leu Ser Pro Phe Gly Arg Leu Phe Val Pro Thr Tyr Ser
        2660                2665                2670

Gly Leu Ala Ser Ser Thr Val Ala Leu Glu Asp Ala Glu Val Ile Ala
```

-continued

```
            2675                2680                2685

Arg Ala Ala Gln Thr Leu Gln Met Asn Ser Val Ser Ile Gln Ser Ser
    2690                2695                2700

Ser Leu Thr Thr Leu Asp Ser Leu Gly Arg Ser Arg Thr Ser Ser Thr
2705                2710                2715                2720

Ala Glu Asp Ser Ser Val Ser Asp Thr Thr Ala Ala Ser His Asp
            2725                2730                2735

Ser Gly Ser Ser Ser Ser Phe Ser Phe Glu Leu Asn Arg Pro Leu
            2740                2745                2750

Ser Glu Thr Glu Leu Gln Phe Ile Lys Ala Leu Ser Ser Leu Lys Ser
            2755                2760                2765

Thr Gln Ala Cys Glu Val Ile Gln Asn Arg Ile Thr Gly Leu Tyr Cys
            2770                2775                2780

Asn Ser Asn Glu Gly Pro Leu Asp Arg His Asn Val Ile Tyr Ser Ser
2785                2790                2795                2800

Arg Met Ala Asp Ser Cys Asp Trp Leu Lys Asp Gly Lys Arg Arg Gly
            2805                2810                2815

Asn Leu Glu Leu Ala Asn Arg Ile Gln Ser Val Leu Cys Ile Leu Ile
            2820                2825                2830

Ala Gly Tyr Tyr Arg Ser Phe Gly Gly Glu Gly Thr Glu Lys Gln Val
            2835                2840                2845

Lys Ala Ser Leu Asn Arg Asp Asp Asn Lys Ile Ile Glu Asp Pro Met
    2850                2855                2860

Ile Gln Leu Ile Pro Glu Lys Leu Arg Arg Glu Leu Glu Arg Leu Gly
2865                2870                2875                2880

Val Ser Arg Met Glu Val Asp Glu Leu Met Pro Ser Ile Ser Pro Asp
            2885                2890                2895

Asp Thr Leu Ala Gln Leu Val Ala Lys Lys Leu Ile Ser Leu Asn Val
            2900                2905                2910

Ser Thr Glu Glu Tyr Ser Ala Glu Val Ser Arg Leu Lys Gln Thr Leu
            2915                2920                2925

Thr Ala Arg Asn Val Leu His Gly Leu Ala Gly Gly Ile Lys Glu Leu
            2930                2935                2940

Ser Leu Pro Ile Tyr Thr Ile Phe Met Lys Ser Tyr Phe Phe Lys Asp
2945                2950                2955                2960

Asn Val Phe Leu Ser Leu Thr Asp Arg Trp Ser Thr Lys His Ser Thr
            2965                2970                2975

Asn Tyr Arg Asp Ser Cys Gly Lys Gln Leu Lys Gly Arg Ile Ile Thr
            2980                2985                2990

Lys Tyr Thr His Trp Leu Asp Thr Phe Leu Gly Cys Ser Val Ser Ile
            2995                3000                3005

Asn Arg His Thr Thr Val Lys Glu Pro Ser Leu Phe Asn Pro Asn Ile
    3010                3015                3020

Arg Cys Val Asn Leu Ile Thr Phe Glu Asp Gly Leu Arg Glu Leu Ser
3025                3030                3035                3040

Val Ile Gln Ser His Leu Lys Val Phe Glu Asn Glu Phe Thr Asn Leu
            3045                3050                3055

Asn Leu Gln Phe Ser Asp Pro Asn Arg Gln Lys Leu Arg Ile Val Glu
            3060                3065                3070

Ser Arg Pro Ala Glu Ser Glu Leu Glu Ala Asn Arg Ala Val Ile Val
            3075                3080                3085

Lys Thr Lys Leu Phe Ser Ala Thr Glu Gln Val Arg Leu Ser Asn Asn
            3090                3095                3100
```

```
Pro Ala Val Val Met Gly Tyr Leu Leu Asp Glu Ser Ala Ile Ser Glu
3105                3110                3115                3120

Val Lys Pro Thr Lys Val Asp Phe Ser Asn Leu Leu Lys Asp Arg Phe
            3125                3130                3135

Lys Ile Met Gln Phe Phe Pro Ser Val Phe Thr Leu Ile Lys Met Leu
        3140                3145                3150

Thr Asp Glu Ser Ser Asp Ser Glu Lys Ser Gly Leu Ser Pro Asp Leu
            3155                3160                3165

Gln Gln Val Ala Arg Tyr Ser Asn His Leu Thr Leu Leu Ser Arg Met
3170                3175                3180

Ile Gln Gln Ala Lys Pro Thr Val Thr Val Phe Tyr Met Leu Lys Gly
3185                3190                3195                3200

Asn Leu Met Asn Thr Glu Pro Thr Val Ala Glu Leu Val Ser Tyr Gly
            3205                3210                3215

Ile Lys Glu Gly Arg Phe Phe Arg Leu Ser Asp Thr Gly Val Asp Ala
            3220                3225                3230

Ser Thr Tyr Ser Val Lys Tyr Trp Lys Ile Leu His Cys Ile Ser Ala
            3235                3240                3245

Ile Gly Cys Leu Pro Leu Ser Gln Ala Asp Lys Ser Ser Leu Leu Met
            3250                3255                3260

Ser Phe Leu Asn Trp Arg Val Asn Met Asp Ile Arg Thr Ser Asp Cys
3265                3270                3275                3280

Pro Leu Ser Ser His Glu Ala Ser Ile Leu Ser Glu Phe Asp Gly Gln
            3285                3290                3295

Val Ile Ala Asn Ile Leu Ala Ser Glu Leu Ser Ser Val Lys Arg Asp
            3300                3305                3310

Ser Glu Arg Glu Gly Leu Thr Asp Leu Leu Asp Tyr Leu Asn Ser Pro
            3315                3320                3325

Thr Glu Leu Leu Lys Lys Lys Pro Tyr Leu Gly Thr Thr Cys Lys Phe
            3330                3335                3340

Asn Thr Trp Gly Asp Ser Asn Arg Ser Gly Lys Phe Thr Tyr Ser Ser
3345                3350                3355                3360

Arg Ser Gly Glu Ser Ile Gly Ile Phe Ile Ala Gly Lys Leu His Ile
            3365                3370                3375

His Leu Ser Ser Glu Ser Val Ala Leu Leu Cys Glu Thr Glu Arg Gln
            3380                3385                3390

Val Leu Ser Trp Met Ser Lys Arg Arg Thr Glu Val Ile Thr Lys Glu
            3395                3400                3405

Gln His Gln Leu Phe Leu Ser Leu Leu Pro Gln Ser His Glu Cys Leu
        3410                3415                3420

Gln Lys His Lys Asp Gly Ser Ala Leu Ser Val Ile Pro Asp Ser Ser
3425                3430                3435                3440

Asn Pro Arg Leu Leu Lys Phe Val Pro Leu Lys Lys Gly Leu Ala Val
            3445                3450                3455

Val Lys Ile Lys Lys Gln Ile Leu Thr Val Lys Lys Gln Val Val Phe
            3460                3465                3470

Asp Ala Glu Ser Glu Pro Arg Leu Gln Trp Gly His Gly Cys Leu Ser
            3475                3480                3485

Ile Val Tyr Asp Glu Thr Asp Thr Gln Thr Thr Tyr His Glu Asn Leu
            3490                3495                3500

Leu Lys Val Lys His Leu Val Asp Cys Ser Thr Asp Arg Lys Lys Leu
3505                3510                3515                3520
```

```
Leu Pro Gln Ser Val Phe Ser Asp Ser Lys Val Val Leu Ser Arg Ile
            3525                3530                3535

Lys Phe Lys Thr Glu Leu Leu Leu Asn Ser Leu Thr Leu Leu His Cys
        3540                3545                3550

Phe Leu Lys His Ala Pro Ser Asp Ala Ile Met Glu Val Glu Ser Lys
        3555                3560                3565

Ser Ser Leu Leu His Lys Tyr Leu Lys Ser Gly Gly Val Arg Gln Arg
        3570                3575                3580

Asn Thr Glu Val Leu Phe Arg Glu Lys Leu Asn Lys Val Val Ile Lys
3585                3590                3595                3600

Asp Asn Leu Glu Gln Gly Val Glu Glu Ile Glu Phe Cys Asn Asn
            3605                3610                3615

Leu Thr Lys Thr Val Ser Glu Asn Pro Leu Pro Leu Ser Cys Trp Ser
            3620                3625                3630

Glu Val Gln Asn Tyr Ile Glu Asp Ile Gly Phe Asn Asn Val Leu Val
            3635                3640                3645

Asn Ile Asp Arg Asn Thr Val Lys Ser Glu Leu Leu Trp Lys Phe Thr
            3650                3655                3660

Leu Asp Thr Asn Val Ser Thr Thr Ser Thr Ile Lys Asp Val Arg Thr
3665                3670                3675                3680

Leu Val Ser Tyr Val Ser Thr Glu Thr Ile Pro Lys Phe Leu Leu Ala
            3685                3690                3695

Phe Leu Leu Tyr Glu Val Leu Met Asn Leu Ile Asn Gln Cys Lys
            3700                3705                3710

Ala Val Lys Glu Leu Ile Asn Ser Thr Gly Leu Ser Asp Leu Glu Leu
            3715                3720                3725

Glu Ser Leu Leu Thr Leu Cys Ala Phe Tyr Phe Gln Ser Glu Cys Ser
            3730                3735                3740

Lys Arg Asp Gly Pro Arg Cys Ser Phe Ala Ala Leu Leu Ser Leu Ile
3745                3750                3755                3760

His Glu Asp Trp Gln Arg Ile Gly Lys Asn Ile Leu Val Arg Ala Asn
            3765                3770                3775

Asn Glu Leu Gly Asp Val Ser Leu Lys Val Asn Ile Val Leu Val Pro
            3780                3785                3790

Leu Lys Asp Met Ser Lys Pro Lys Ser Glu Arg Val Val Met Ala Arg
            3795                3800                3805

Arg Ser Leu Asn His Ala Leu Ser Leu Met Phe Leu Asp Glu Met Ser
            3810                3815                3820

Leu Pro Glu Leu Lys Ser Leu Ser Val Asn Cys Lys Met Gly Asn Phe
3825                3830                3835                3840

Glu Gly Gln Glu Cys Phe Glu Phe Thr Ile Leu Lys Asp Asn Ser Ala
            3845                3850                3855

Arg Leu Asp Tyr Asn Lys Leu Ile Asp His Cys Val Asp Met Glu Lys
            3860                3865                3870

Lys Arg Glu Ala Val Arg Ala Val Glu Asp Leu Ile Leu Met Leu Thr
            3875                3880                3885

Gly Arg Ala Val Lys Pro Ser Ala Val Thr Gln Phe Val His Gly Asp
            3890                3895                3900

Glu Gln Cys Gln Glu Gln Ile Ser Leu Asp Asp Leu Met Ala Asn Asp
3905                3910                3915                3920

Thr Val Thr Asp Phe Pro Asp Arg Glu Ala Glu Ala Leu Lys Thr Gly
            3925                3930                3935

Asn Leu Gly Phe Asn Trp Asp Ser Asp
```

```
                        3940                3945
```

<210> SEQ ID NO 2
<211> LENGTH: 1684
<212> TYPE: PRT
<213> ORGANISM: Nairovirus
<220> FEATURE:
<223> OTHER INFORMATION: Nairovirus Crimean-Congo hemorrhagic fever
      virus (CCHFV) M (Middle) protein, envelope proteins Ge
      and Gn glycoprotein precursor

<400> SEQUENCE: 2

Met His Ile Ser Leu Met Tyr Ala Ile Leu Cys Leu Gln Leu Cys Gly
 1               5                  10                  15

Leu Gly Glu Thr His Gly Ser His Asn Glu Thr Arg His Asn Lys Thr
            20                  25                  30

Asp Thr Met Thr Thr Pro Gly Asp Asn Pro Ser Ser Glu Pro Pro Val
        35                  40                  45

Ser Thr Ala Leu Ser Ile Thr Leu Asp Pro Ser Thr Val Thr Pro Thr
    50                  55                  60

Thr Pro Ala Ser Gly Leu Glu Gly Ser Gly Glu Val Tyr Thr Ser Pro
65                  70                  75                  80

Pro Ile Thr Thr Gly Ser Leu Pro Leu Ser Glu Thr Thr Pro Glu Leu
                85                  90                  95

Pro Val Thr Thr Gly Thr Asp Thr Leu Ser Ala Gly Asp Val Asp Pro
            100                 105                 110

Ser Thr Gln Thr Ala Gly Gly Thr Ser Ala Pro Thr Val Arg Thr Ser
        115                 120                 125

Leu Pro Asn Ser Pro Ser Thr Pro Ser Thr Pro Gln Asp Thr His His
    130                 135                 140

Pro Val Arg Asn Leu Leu Ser Val Thr Ser Pro Gly Pro Asp Glu Thr
145                 150                 155                 160

Ser Thr Pro Ser Gly Thr Gly Lys Glu Ser Ser Ala Thr Ser Ser Pro
                165                 170                 175

His Pro Val Ser Asn Arg Pro Pro Thr Pro Pro Ala Thr Ala Gln Gly
            180                 185                 190

Pro Thr Glu Asn Asp Ser His Asn Ala Thr Glu His Pro Glu Ser Leu
        195                 200                 205

Thr Gln Ser Ala Thr Pro Gly Leu Met Thr Ser Pro Thr Gln Ile Val
    210                 215                 220

His Pro Gln Ser Ala Thr Pro Ile Thr Val Gln Asp Thr His Pro Ser
225                 230                 235                 240

Pro Thr Asn Arg Ser Lys Arg Asn Leu Lys Met Glu Ile Ile Leu Thr
                245                 250                 255

Leu Ser Gln Gly Leu Lys Lys Tyr Tyr Gly Lys Ile Leu Arg Leu Leu
            260                 265                 270

Gln Leu Thr Leu Glu Glu Asp Thr Glu Gly Leu Leu Glu Trp Cys Lys
        275                 280                 285

Arg Asn Leu Gly Leu Asp Cys Asp Asp Thr Phe Phe Gln Lys Arg Ile
    290                 295                 300

Glu Glu Phe Phe Ile Thr Gly Glu Gly His Phe Asn Glu Val Leu Gln
305                 310                 315                 320

Phe Arg Thr Pro Gly Thr Leu Ser Thr Thr Glu Ser Thr Pro Ala Gly
                325                 330                 335

Leu Pro Thr Ala Glu Pro Phe Lys Ser Tyr Phe Ala Lys Gly Phe Leu
            340                 345                 350

```
Ser Ile Asp Ser Gly Tyr Tyr Ser Ala Lys Cys Tyr Ser Gly Thr Ser
        355                 360                 365
Asn Ser Gly Leu Gln Leu Ile Asn Ile Thr Arg His Ser Thr Arg Ile
        370                 375                 380
Val Asp Thr Pro Gly Pro Lys Ile Thr Asn Leu Lys Thr Ile Asn Cys
385                 390                 395                 400
Ile Asn Leu Lys Ala Ser Ile Phe Lys Glu His Arg Glu Val Glu Ile
                405                 410                 415
Asn Val Leu Leu Pro Gln Val Ala Val Asn Leu Ser Asn Cys His Val
                420                 425                 430
Val Ile Lys Ser His Val Cys Asp Tyr Ser Leu Asp Ile Asp Gly Ala
        435                 440                 445
Val Arg Leu Pro His Ile Tyr His Glu Gly Val Phe Ile Pro Gly Thr
        450                 455                 460
Tyr Lys Ile Val Ile Asp Lys Lys Asn Lys Leu Asn Asp Arg Cys Thr
465                 470                 475                 480
Leu Phe Thr Asp Cys Val Ile Lys Gly Arg Glu Val Arg Lys Gly Gln
                485                 490                 495
Ser Val Leu Arg Gln Tyr Lys Thr Glu Ile Arg Ile Gly Lys Ala Ser
                500                 505                 510
Thr Gly Ser Arg Arg Leu Leu Ser Glu Glu Pro Ser Asp Asp Cys Ile
        515                 520                 525
Ser Arg Thr Gln Leu Leu Arg Thr Glu Thr Ala Glu Ile His Gly Asp
        530                 535                 540
Asn Tyr Gly Gly Pro Gly Asp Lys Ile Thr Ile Cys Asn Gly Ser Thr
545                 550                 555                 560
Ile Val Asp Gln Arg Leu Gly Ser Glu Leu Gly Cys Tyr Thr Ile Asn
                565                 570                 575
Arg Val Arg Ser Phe Lys Leu Cys Glu Asn Ser Ala Thr Gly Lys Asn
                580                 585                 590
Cys Glu Ile Asp Ser Val Pro Val Lys Cys Arg Gln Gly Tyr Cys Leu
        595                 600                 605
Arg Ile Thr Gln Glu Gly Arg Gly His Val Lys Leu Ser Arg Gly Ser
        610                 615                 620
Glu Val Val Leu Asp Ala Cys Asp Thr Ser Cys Glu Ile Met Ile Pro
625                 630                 635                 640
Lys Gly Thr Gly Asp Ile Leu Val Asp Cys Ser Gly Gly Gln Gln His
                645                 650                 655
Phe Leu Lys Asp Asn Leu Ile Asp Leu Gly Cys Pro Lys Ile Pro Leu
                660                 665                 670
Leu Gly Lys Met Ala Ile Tyr Ile Cys Arg Met Ser Asn His Pro Lys
        675                 680                 685
Thr Thr Met Ala Phe Leu Phe Trp Phe Ser Phe Gly Tyr Val Ile Thr
        690                 695                 700
Cys Ile Leu Cys Lys Ala Ile Phe Tyr Leu Leu Ile Ile Val Gly Thr
705                 710                 715                 720
Leu Gly Lys Arg Leu Lys Gln Tyr Arg Glu Leu Lys Pro Gln Thr Cys
                725                 730                 735
Thr Ile Cys Glu Thr Thr Pro Val Asn Ala Ile Asp Ala Glu Met His
                740                 745                 750
Asp Leu Asn Cys Ser Tyr Asn Ile Cys Pro Tyr Cys Ala Ser Arg Leu
        755                 760                 765
```

```
Thr Ser Asp Gly Leu Ala Arg His Val Ile Gln Cys Pro Lys Arg Lys
    770                 775                 780

Glu Lys Val Glu Thr Glu Leu Tyr Leu Asn Leu Glu Arg Ile Pro
785                 790                 795                 800

Trp Val Val Arg Lys Leu Leu Gln Val Ser Glu Ser Thr Gly Val Ala
                    805                 810                 815

Leu Lys Arg Ser Ser Trp Leu Ile Val Leu Val Leu Phe Thr Val
                820                 825                 830

Ser Leu Ser Pro Val Gln Ser Ala Pro Ile Gly Gln Gly Lys Thr Ile
            835                 840                 845

Glu Ala Tyr Arg Ala Arg Glu Gly Tyr Thr Ser Ile Cys Leu Phe Val
850                 855                 860

Leu Gly Ser Ile Leu Phe Ile Val Ser Cys Leu Met Lys Gly Leu Val
865                 870                 875                 880

Asp Ser Val Gly Asn Ser Phe Phe Pro Gly Leu Ser Ile Cys Lys Thr
                885                 890                 895

Cys Ser Ile Ser Ser Ile Asn Gly Phe Glu Ile Glu Ser His Lys Cys
            900                 905                 910

Tyr Cys Ser Leu Phe Cys Cys Pro Tyr Cys Arg His Cys Ser Thr Asp
        915                 920                 925

Lys Glu Ile His Lys Leu His Leu Ser Ile Cys Lys Lys Arg Lys Lys
    930                 935                 940

Gly Ser Asn Val Met Leu Ala Val Cys Lys Leu Met Cys Phe Arg Ala
945                 950                 955                 960

Thr Met Glu Val Ser Asn Arg Ala Leu Phe Ile Arg Ser Ile Ile Asn
                965                 970                 975

Thr Thr Phe Val Leu Cys Ile Leu Ile Leu Ala Val Cys Val Val Ser
                980                 985                 990

Thr Ser Ala Val Glu Met Glu Asn Leu Pro Ala Gly Thr Trp Glu Arg
            995                 1000                1005

Glu Glu Asp Leu Thr Asn Phe Cys His Gln Cys Gln Val Thr Glu
    1010                1015                1020

Thr Glu Cys Leu Cys Pro Tyr Glu Ala Leu Val Leu Arg Lys Pro Leu
1025                1030                1035                1040

Phe Leu Asp Ser Thr Ala Lys Gly Met Lys Asn Leu Leu Asn Ser Thr
                1045                1050                1055

Ser Leu Glu Thr Ser Leu Ser Ile Glu Ala Pro Trp Gly Ala Ile Asn
            1060                1065                1070

Val Gln Ser Thr Tyr Lys Pro Thr Val Ser Thr Ala Asn Ile Ala Leu
        1075                1080                1085

Ser Trp Ser Ser Val Glu His Arg Gly Asn Lys Ile Leu Val Ser Gly
    1090                1095                1100

Arg Ser Glu Ser Ile Met Lys Leu Glu Glu Arg Thr Gly Ile Ser Trp
1105                1110                1115                1120

Asp Leu Gly Val Glu Asp Ala Ser Glu Ser Lys Leu Leu Thr Val Ser
                1125                1130                1135

Val Met Asp Leu Ser Gln Met Tyr Ser Pro Val Phe Glu Tyr Leu Ser
                1140                1145                1150

Gly Asp Arg Gln Val Gly Glu Trp Pro Lys Ala Thr Cys Thr Gly Asp
            1155                1160                1165

Cys Pro Glu Arg Cys Gly Cys Thr Ser Ser Thr Cys Leu His Lys Glu
    1170                1175                1180

Trp Pro His Ser Arg Asn Trp Arg Cys Asn Pro Thr Trp Cys Trp Gly
```

```
                1185              1190              1195              1200
Val Gly Thr Gly Cys Thr Cys Cys Gly Leu Asp Val Lys Asp Leu Phe
                    1205              1210              1215

Thr Asp Tyr Met Phe Val Lys Trp Lys Val Glu Tyr Ile Lys Thr Glu
                    1220              1225              1230

Ala Ile Val Cys Val Glu Leu Thr Ser Gln Glu Arg Gln Cys Ser Leu
                    1235              1240              1245

Ile Glu Ala Gly Thr Arg Phe Asn Leu Gly Pro Val Thr Ile Thr Leu
                    1250              1255              1260

Ser Glu Pro Arg Asn Ile Gln Gln Lys Leu Pro Pro Glu Ile Ile Thr
1265              1270              1275              1280

Leu His Pro Arg Ile Glu Glu Gly Phe Phe Asp Leu Met His Val Gln
                    1285              1290              1295

Lys Val Leu Ser Ala Ser Thr Val Cys Lys Leu Gln Ser Cys Thr His
                    1300              1305              1310

Gly Val Pro Gly Asp Leu Gln Val Tyr His Ile Gly Asn Leu Leu Lys
                    1315              1320              1325

Gly Asp Lys Val Asn Gly His Leu Ile His Lys Ile Glu Pro His Phe
                    1330              1335              1340

Asn Thr Ser Trp Met Ser Trp Asp Gly Cys Asp Leu Asp Tyr Tyr Cys
1345              1350              1355              1360

Asn Met Gly Asp Trp Pro Ser Cys Thr Tyr Thr Gly Val Thr Gln His
                    1365              1370              1375

Asn His Ala Ser Phe Val Asn Leu Leu Asn Ile Glu Thr Asp Tyr Thr
                    1380              1385              1390

Lys Asn Phe His Phe His Ser Lys Arg Val Thr Ala His Gly Asp Thr
                    1395              1400              1405

Pro Gln Leu Asp Leu Lys Ala Arg Pro Thr Tyr Gly Ala Gly Glu Ile
                    1410              1415              1420

Thr Val Leu Val Glu Val Ala Asp Met Glu Leu His Thr Lys Lys Ile
1425              1430              1435              1440

Glu Ile Ser Gly Leu Lys Phe Ala Ser Leu Ala Cys Thr Gly Cys Tyr
                    1445              1450              1455

Ala Cys Ser Ser Gly Ile Ser Cys Lys Val Arg Ile His Val Asp Glu
                    1460              1465              1470

Pro Asp Glu Leu Thr Val His Val Lys Ser Asp Pro Asp Val Val
                    1475              1480              1485

Ala Ala Ser Ser Ser Leu Met Ala Arg Lys Leu Glu Phe Gly Thr Asp
                    1490              1495              1500

Ser Thr Phe Lys Ala Phe Ser Ala Met Pro Lys Thr Ser Leu Cys Phe
1505              1510              1515              1520

Tyr Ile Val Glu Arg Glu His Cys Lys Ser Cys Ser Glu Glu Asp Thr
                    1525              1530              1535

Lys Lys Cys Val Asn Thr Lys Leu Glu Gln Pro Gln Ser Ile Leu Ile
                    1540              1545              1550

Glu His Lys Gly Thr Ile Ile Gly Lys Gln Asn Ser Thr Cys Thr Ala
                    1555              1560              1565

Lys Ala Ser Cys Trp Leu Glu Ser Val Lys Ser Phe Phe Tyr Gly Leu
                    1570              1575              1580

Lys Asn Met Leu Ser Gly Ile Phe Gly Asn Val Phe Met Gly Ile Phe
1585              1590              1595              1600

Leu Phe Leu Ala Pro Phe Ile Leu Leu Ile Leu Phe Phe Met Phe Gly
                    1605              1610              1615
```

```
Trp Arg Ile Leu Phe Cys Phe Lys Cys Cys Arg Arg Thr Arg Gly Leu
            1620                1625                1630

Phe Lys Tyr Arg His Leu Lys Asp Asp Glu Glu Thr Gly Tyr Arg Arg
        1635                1640                1645

Ile Ile Glu Lys Leu Asn Asn Lys Lys Gly Lys Asn Lys Leu Leu Asp
    1650                1655                1660

Gly Glu Arg Leu Ala Asp Arg Arg Ile Ala Glu Leu Phe Ser Thr Lys
1665                1670                1675                1680

Thr His Ile Gly

<210> SEQ ID NO 3
<211> LENGTH: 482
<212> TYPE: PRT
<213> ORGANISM: Nairovirus
<220> FEATURE:
<223> OTHER INFORMATION: Nairovirus Crimean-Congo hemorrhagic fever
      virus (CCHFV) S (Small) protein, nucleocapsid protein

<400> SEQUENCE: 3

Met Glu Asn Lys Ile Glu Val Asn Asn Lys Asp Glu Met Asn Arg Trp
 1               5                   10                  15

Phe Glu Glu Phe Lys Lys Gly Asn Gly Leu Val Asp Thr Phe Thr Asn
                20                  25                  30

Ser Tyr Ser Phe Cys Glu Ser Val Pro Asn Leu Asp Arg Phe Val Phe
            35                  40                  45

Gln Met Ala Ser Ala Thr Asp Asp Ala Gln Lys Asp Ser Ile Tyr Ala
        50                  55                  60

Ser Ala Leu Val Glu Ala Thr Lys Phe Cys Ala Pro Ile Tyr Glu Cys
65                  70                  75                  80

Ala Trp Val Ser Ser Thr Gly Ile Val Lys Lys Gly Leu Glu Trp Phe
                85                  90                  95

Glu Lys Asn Ala Gly Thr Ile Lys Ser Trp Asp Glu Ser Tyr Thr Glu
                100                 105                 110

Leu Lys Val Asp Val Pro Lys Ile Glu Gln Leu Thr Gly Tyr Gln Gln
            115                 120                 125

Ala Ala Leu Lys Trp Arg Lys Asp Ile Gly Phe Arg Val Asn Ala Asn
        130                 135                 140

Thr Ala Ala Leu Ser Asn Lys Val Leu Ala Glu Tyr Lys Val Pro Gly
145                 150                 155                 160

Glu Ile Val Met Ser Val Lys Glu Met Leu Ser Asp Met Ile Arg Arg
                165                 170                 175

Arg Asn Leu Ile Leu Asn Arg Gly Gly Asp Glu Asn Pro Arg Gly Pro
                180                 185                 190

Val Ser His Glu His Val Asp Trp Cys Arg Glu Phe Val Lys Gly Lys
            195                 200                 205

Tyr Ile Met Ala Phe Asn Pro Pro Trp Gly Asp Ile Asn Lys Ser Gly
        210                 215                 220

Arg Ser Gly Ile Ala Leu Val Ala Thr Gly Leu Ala Lys Leu Ala Glu
225                 230                 235                 240

Thr Glu Gly Lys Gly Ile Phe Asp Glu Ala Lys Lys Thr Val Glu Ala
                245                 250                 255

Leu Asn Gly Tyr Leu Asp Lys His Lys Asp Glu Val Asp Arg Ala Ser
                260                 265                 270

Ala Asp Ser Met Ile Thr Asn Leu Leu Lys His Ile Ala Lys Ala Gln
            275                 280                 285
```

```
Glu Leu Tyr Lys Asn Ser Ser Ala Leu Arg Ala Gln Ser Ala Gln Ile
        290                 295                 300

Asp Thr Ala Phe Ser Ser Tyr Tyr Trp Leu Tyr Lys Ala Gly Val Thr
305                 310                 315                 320

Pro Glu Thr Phe Pro Thr Val Ser Gln Phe Leu Phe Glu Leu Gly Lys
                325                 330                 335

Gln Pro Arg Gly Thr Lys Lys Met Lys Lys Ala Leu Leu Ser Thr Pro
                340                 345                 350

Met Lys Trp Gly Lys Lys Leu Tyr Glu Leu Phe Ala Asp Asp Ser Phe
            355                 360                 365

Gln Gln Asn Arg Ile Tyr Met His Pro Ala Val Leu Thr Ala Gly Arg
        370                 375                 380

Ile Ser Glu Met Gly Val Cys Phe Gly Thr Ile Pro Val Ala Asn Pro
385                 390                 395                 400

Asp Asp Ala Ala Gln Gly Ser Gly His Thr Lys Ser Ile Leu Asn Leu
                405                 410                 415

Arg Thr Asn Thr Glu Thr Asn Asn Pro Cys Ala Lys Thr Ile Val Lys
                420                 425                 430

Leu Phe Glu Val Gln Lys Thr Gly Phe Asn Ile Gln Asp Met Asp Ile
            435                 440                 445

Val Ala Ser Glu His Leu Leu His Gln Ser Leu Val Gly Lys Gln Ser
        450                 455                 460

Pro Phe Gln Asn Ala Tyr Asn Val Lys Gly Asn Ala Thr Ser Ala Asn
465                 470                 475                 480

Ile Ile

<210> SEQ ID NO 4
<211> LENGTH: 7
<212> TYPE: PRT
<213> ORGANISM: Artificial Sequence
<220> FEATURE:
<223> OTHER INFORMATION: synthetic Nairovirus Crimean-Congo hemorrhagic
      fever virus (CCHFV) Afg09-2990 strain L (Large)
      protein conserved region

<400> SEQUENCE: 4

Trp Thr Gln Val Ile Asp Gly
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic Nairovirus Crimean-Congo hemorrhagic
      fever virus (CCHFV)  Afg09-2990, Matin, Oman,
      Baghdad, UG3010, Turkey and SPU128-81 strains L
      (Large) protein conserved region

<400> SEQUENCE: 5

Glu Glu Pro Glu Ala Lys Leu
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic Nairovirus Crimean-Congo hemorrhagic
      fever virus (CCHFV) Matin strain L (Large) protein
      conserved region
```

```
<400> SEQUENCE: 6

Trp Thr Gln Val Ile Asp Ser
 1               5

<210> SEQ ID NO 7
<211> LENGTH: 7
<212> TYPE: PRT
<213> ORGANISM: Artificial Sequence
<220> FEATURE:
<223> OTHER INFORMATION: synthetic Nairovirus Crimean-Congo hemorrhagic
      fever virus (CCHFV) Oman, UG3010, IbAr10200 and
      SPU128-81 strains L (Large) protein conserved
      region

<400> SEQUENCE: 7

Trp Thr Gln Val Ile Ala Gly
 1               5

<210> SEQ ID NO 8
<211> LENGTH: 7
<212> TYPE: PRT
<213> ORGANISM: Artificial Sequence
<220> FEATURE:
<223> OTHER INFORMATION: synthetic Nairovirus Crimean-Congo hemorrhagic
      fever virus (CCHFV) Baghdad strain L (Large)
      protein conserved region

<400> SEQUENCE: 8

Trp Thr Gln Val Met Ala Gly
 1               5

<210> SEQ ID NO 9
<211> LENGTH: 7
<212> TYPE: PRT
<213> ORGANISM: Artificial Sequence
<220> FEATURE:
<223> OTHER INFORMATION: synthetic Nairovirus Crimean-Congo hemorrhagic
      fever virus (CCHFV) Turkey strain L (Large)
      protein conserved region

<400> SEQUENCE: 9

Trp Thr Gln Val Ile Ala Ser
 1               5

<210> SEQ ID NO 10
<211> LENGTH: 7
<212> TYPE: PRT
<213> ORGANISM: Artificial Sequence
<220> FEATURE:
<223> OTHER INFORMATION: synthetic Nairovirus Crimean-Congo hemorrhagic
      fever virus (CCHFV) IbAr10200 strain L (Large)
      protein conserved region

<400> SEQUENCE: 10

Glu Glu Pro Glu Ala Arg Leu
 1               5

<210> SEQ ID NO 11
<211> LENGTH: 7
<212> TYPE: PRT
<213> ORGANISM: Artificial Sequence
<220> FEATURE:
<223> OTHER INFORMATION: synthetic Nairovirus Crimean-Congo hemorrhagic
      fever virus (CCHFV) AP92Greece strain L (Large)
      protein conserved region

<400> SEQUENCE: 11
```

```
Trp Thr Gln Val Leu Ala Gly
 1               5
```

<210> SEQ ID NO 12
<211> LENGTH: 7
<212> TYPE: PRT
<213> ORGANISM: Artificial Sequence
<220> FEATURE:
<223> OTHER INFORMATION: synthetic Nairovirus Crimean-Congo hemorrhagic
      fever virus (CCHFV) AP92Greece strain L (Large)
      protein conserved region

<400> SEQUENCE: 12

```
Asp Glu Pro Glu Ala Lys Leu
 1               5
```

<210> SEQ ID NO 13
<211> LENGTH: 7
<212> TYPE: PRT
<213> ORGANISM: Artificial Sequence
<220> FEATURE:
<223> OTHER INFORMATION: synthetic Nairovirus Dugbe virus (DUGV) L
      (Large) protein conserved region

<400> SEQUENCE: 13

```
Trp Glu Arg Val Val Asp Glu
 1               5
```

<210> SEQ ID NO 14
<211> LENGTH: 8
<212> TYPE: PRT
<213> ORGANISM: Artificial Sequence
<220> FEATURE:
<223> OTHER INFORMATION: synthetic Nairovirus Dugbe virus (DUGV) L
      (Large) protein conserved region

<400> SEQUENCE: 14

```
Thr Glu Pro Glu Ala Val Gly Thr
 1               5
```

<210> SEQ ID NO 15
<211> LENGTH: 8
<212> TYPE: PRT
<213> ORGANISM: Artificial Sequence
<220> FEATURE:
<223> OTHER INFORMATION: synthetic Nairovirus Crimean-Congo hemorrhagic
      fever virus (CCHFV) L (Large) protein conserved
      region

<400> SEQUENCE: 15

```
Glu Glu Pro Glu Ala Arg Leu Val
 1               5
```

<210> SEQ ID NO 16
<211> LENGTH: 7
<212> TYPE: PRT
<213> ORGANISM: Artificial Sequence
<220> FEATURE:
<223> OTHER INFORMATION: synthetic Nairovirus Nairobi sheep disease
      virus (NSDV) L (Large) protein conserved region

<400> SEQUENCE: 16

```
Trp Glu Glu Val Val Pro Gly
 1               5
```

<210> SEQ ID NO 17
<211> LENGTH: 8
<212> TYPE: PRT

```
<213> ORGANISM: Artificial Sequence
<220> FEATURE:
<223> OTHER INFORMATION: synthetic Nairovirus Nairobi sheep disease
      virus (NSDV) L (Large) protein conserved region

<400> SEQUENCE: 17

Glu Glu Pro Glu Ala Lys Gly Leu
 1               5

<210> SEQ ID NO 18
<211> LENGTH: 6
<212> TYPE: PRT
<213> ORGANISM: Artificial Sequence
<220> FEATURE:
<223> OTHER INFORMATION: synthetic Nairovirus Erve virus (ERVEV) L
      (Large) protein conserved region

<400> SEQUENCE: 18

Trp Glu Asn Ile Glu Gly
 1               5

<210> SEQ ID NO 19
<211> LENGTH: 8
<212> TYPE: PRT
<213> ORGANISM: Artificial Sequence
<220> FEATURE:
<223> OTHER INFORMATION: synthetic Nairovirus Erve virus (ERVEV) L
      (Large) protein conserved region

<400> SEQUENCE: 19

Ile Glu Pro Glu Ala Ile Gly Leu
 1               5

<210> SEQ ID NO 20
<211> LENGTH: 7
<212> TYPE: PRT
<213> ORGANISM: Artificial Sequence
<220> FEATURE:
<223> OTHER INFORMATION: synthetic Nairovirus Hazara virus (HAZV) L
      (Large) protein conserved region

<400> SEQUENCE: 20

Trp Asp Ser Val Ser Asp Ile
 1               5

<210> SEQ ID NO 21
<211> LENGTH: 8
<212> TYPE: PRT
<213> ORGANISM: Artificial Sequence
<220> FEATURE:
<223> OTHER INFORMATION: synthetic Nairovirus Hazara virus (HAZV) L
      (Large) protein conserved region

<400> SEQUENCE: 21

Thr Glu Pro Glu Ala Ala Ala Thr
 1               5

<210> SEQ ID NO 22
<211> LENGTH: 6
<212> TYPE: PRT
<213> ORGANISM: Artificial Sequence
<220> FEATURE:
<223> OTHER INFORMATION: synthetic ubiquitin substrate carboxy terminal
      of ubuquitin hexapeptide homolog
<220> FEATURE:
<221> NAME/KEY: MOD_RES
<222> LOCATION: (6)...(6)
<223> OTHER INFORMATION: Gly modified by 7-amino-4-methylcoumarin (AMC)
      fluorescent tag
```

```
<400> SEQUENCE: 22

Glx Arg Leu Arg Gly Gly
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic ubiquitin substrate carboxy terminal
      of ubuquitin hexapeptide homolog

<400> SEQUENCE: 23

Glx Arg Leu Arg Gly Gly
1               5
```